(12) United States Patent
Stahmann et al.

(10) Patent No.: US 7,575,553 B2
(45) Date of Patent: Aug. 18, 2009

(54) METHODS AND SYSTEMS FOR ASSESSING PULMONARY DISEASE

(75) Inventors: Jeffrey E. Stahmann, Ramsey, MN (US); Jesse W. Hartley, Lino Lakes, MN (US); Kent Lee, Fridley, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 507 days.

(21) Appl. No.: 10/930,508

(22) Filed: Aug. 31, 2004

(65) Prior Publication Data

US 2005/0065448 A1    Mar. 24, 2005

Related U.S. Application Data

(60) Provisional application No. 60/504,711, filed on Sep. 18, 2003.

(51) Int. Cl.
*A61B 5/08* (2006.01)
(52) U.S. Cl. ........................ 600/528; 600/538
(58) Field of Classification Search .......... 600/529–543
See application file for complete search history.

(56) References Cited

U.S. PATENT DOCUMENTS

| | | | |
|---|---|---|---|
| 4,312,734 A | 1/1982 | Nichols | |
| 4,365,636 A | 12/1982 | Barker | |
| 4,390,405 A | 6/1983 | Hahn et al. | |
| 4,562,841 A | 1/1986 | Brockway et al. | |
| 4,702,253 A | 10/1987 | Nappholz et al. | |
| 4,721,110 A | 1/1988 | Lampadius | |
| 4,777,962 A | 10/1988 | Watson et al. | |
| 4,802,485 A | 2/1989 | Bowers et al. | |
| 4,807,629 A | 2/1989 | Baudino et al. | |
| 4,813,427 A | 3/1989 | Schlaefke et al. | |
| 4,827,935 A | 5/1989 | Geddes et al. | |
| 4,830,008 A | 5/1989 | Meer | |
| 4,836,219 A | 6/1989 | Hobson et al. | |
| 4,856,524 A | 8/1989 | Baker, Jr. | |
| 4,875,477 A | 10/1989 | Waschke et al. | |

(Continued)

FOREIGN PATENT DOCUMENTS

EP    0750920    1/1997

(Continued)

OTHER PUBLICATIONS

Mansfield, D. et al., *Effects of Continuous Positive Airway Pressure on Lung Function in Patients with Chronic Obstructive Pulmonary Disease and Sleep Disordered Breathing*, Respirology 365-70 (1999).

(Continued)

*Primary Examiner*—Patricia C Mallari
*Assistant Examiner*—Karen E Toth
(74) *Attorney, Agent, or Firm*—Hollingsworth & Funk, LLC

(57) ABSTRACT

Sensing physiological conditions using the sensors of a respiratory therapy device can be used to assess a presence of pulmonary diseases other than breathing rhythm disorders. Non-rhythm related pulmonary diseases include, for example, obstructive pulmonary diseases, restrictive pulmonary diseases, and infectious diseases. Various pulmonary diseases will produce changes in respiratory pressure, airflow, and/or other patient conditions, facilitating assessment of a presence of disease.

25 Claims, 33 Drawing Sheets

U.S. PATENT DOCUMENTS

| | | |
|---|---|---|
| 4,886,064 A | 12/1989 | Strandberg |
| 4,928,688 A | 5/1990 | Mower |
| 4,958,632 A | 9/1990 | Duggan |
| 4,961,423 A | 10/1990 | Canducci |
| 4,982,738 A | 1/1991 | Griebel |
| 5,024,222 A | 6/1991 | Thacker |
| 5,036,849 A | 8/1991 | Hauck et al. |
| 5,047,930 A | 9/1991 | Martens et al. |
| 5,105,354 A | 4/1992 | Nishimura |
| 5,123,425 A | 6/1992 | Shannon, Jr. et al. |
| 5,146,918 A | 9/1992 | Kallok et al. |
| 5,174,287 A | 12/1992 | Kallok et al. |
| 5,178,156 A | 1/1993 | Takishima et al. |
| 5,183,038 A | 2/1993 | Hoffman et al. |
| 5,187,657 A | 2/1993 | Forbes |
| 5,199,424 A | 4/1993 | Sullivan et al. |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,243,979 A | 9/1993 | Stein et al. |
| 5,245,995 A | 9/1993 | Sullivan et al. |
| 5,259,373 A | 11/1993 | Gruenke et al. |
| 5,275,159 A | 1/1994 | Griebel |
| 5,280,791 A | 1/1994 | Lavie |
| 5,284,136 A | 2/1994 | Hauck et al. |
| 5,299,118 A | 3/1994 | Martens et al. |
| 5,301,677 A | 4/1994 | Hsung |
| 5,313,953 A | 5/1994 | Yomtov et al. |
| 5,334,222 A | 8/1994 | Salo et al. |
| 5,335,657 A | 8/1994 | Terry, Jr. et al. |
| 5,353,788 A | 10/1994 | Miles |
| 5,360,442 A | 11/1994 | Dahl et al. |
| 5,363,842 A * | 11/1994 | Mishelevich et al. ... 128/200.14 |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,398,682 A | 3/1995 | Lynn |
| 5,404,877 A | 4/1995 | Nolan et al. |
| 5,411,031 A | 5/1995 | Yomtov |
| 5,466,245 A | 11/1995 | Spinelli et al. |
| 5,483,969 A | 1/1996 | Testerman et al. |
| 5,485,851 A | 1/1996 | Erickson |
| 5,487,755 A | 1/1996 | Snell et al. |
| 5,517,983 A | 5/1996 | Deighan et al. |
| 5,520,176 A | 5/1996 | Cohen |
| 5,522,382 A | 6/1996 | Sullivan et al. |
| 5,522,862 A | 6/1996 | Testerman et al. |
| 5,540,727 A | 7/1996 | Tockman et al. |
| 5,545,186 A | 8/1996 | Olson et al. |
| 5,545,202 A | 8/1996 | Dahl et al. |
| 5,549,655 A | 8/1996 | Erickson |
| 5,590,648 A | 1/1997 | Mitchell et al. |
| 5,593,431 A | 1/1997 | Sheldon |
| 5,603,732 A | 2/1997 | Dahl et al. |
| 5,605,151 A | 2/1997 | Lynn |
| 5,632,281 A * | 5/1997 | Rayburn .................. 600/532 |
| 5,645,570 A | 7/1997 | Corbucci |
| 5,693,000 A | 12/1997 | Crosby et al. |
| 5,697,951 A | 12/1997 | Harpstead et al. |
| 5,701,894 A | 12/1997 | Cherry et al. |
| 5,704,345 A * | 1/1998 | Berthon-Jones ........ 128/204.23 |
| 5,713,933 A | 2/1998 | Condie et al. |
| 5,715,812 A | 2/1998 | Deighan et al. |
| 5,720,771 A | 2/1998 | Snell |
| 5,738,102 A | 4/1998 | Lemelson |
| 5,792,188 A | 8/1998 | Starkweather et al. |
| 5,794,615 A | 8/1998 | Estes |
| 5,800,470 A | 9/1998 | Stein et al. |
| 5,802,188 A | 9/1998 | McDonough |
| 5,814,087 A | 9/1998 | Renirie |
| 5,826,579 A | 10/1998 | Remmers et al. |
| 5,836,987 A | 11/1998 | Baumann et al. |
| 5,839,430 A * | 11/1998 | Cama .................. 128/200.14 |
| 5,844,680 A | 12/1998 | Sperling |
| 5,855,593 A | 1/1999 | Olson et al. |
| 5,861,011 A | 1/1999 | Stoop |
| 5,891,023 A | 4/1999 | Lynn |
| 5,902,250 A | 5/1999 | Verrier et al. |
| 5,911,218 A | 6/1999 | DiMarco |
| 5,916,243 A | 6/1999 | KenKnight et al. |
| 5,944,680 A | 8/1999 | Christopherson et al. |
| 5,957,861 A | 9/1999 | Combs et al. |
| 5,964,778 A | 10/1999 | Fugoso et al. |
| 5,970,975 A | 10/1999 | Estes et al. |
| 5,974,340 A | 10/1999 | Kadhiresan |
| 5,974,349 A | 10/1999 | Levine |
| 5,981,011 A | 11/1999 | Overcash et al. |
| 6,015,388 A | 1/2000 | Sackner et al. |
| 6,021,351 A | 2/2000 | Kadhiresan et al. |
| 6,026,320 A | 2/2000 | Carlson et al. |
| 6,044,297 A | 3/2000 | Sheldon et al. |
| 6,044,298 A | 3/2000 | Salo et al. |
| 6,045,513 A | 4/2000 | Stone et al. |
| 6,047,203 A | 4/2000 | Sackner et al. |
| 6,055,454 A | 4/2000 | Heemels |
| 6,059,725 A | 5/2000 | Steinschneider |
| 6,064,910 A | 5/2000 | Andersson et al. |
| 6,076,015 A | 6/2000 | Hartley et al. |
| 6,091,973 A | 7/2000 | Colla et al. |
| 6,091,986 A | 7/2000 | Keimel |
| 6,099,479 A | 8/2000 | Christopherson et al. |
| 6,105,575 A | 8/2000 | Estes et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,144,866 A | 11/2000 | Miesel et al. |
| 6,148,814 A * | 11/2000 | Clemmer et al. ....... 128/200.24 |
| 6,155,976 A | 12/2000 | Sackner et al. |
| 6,161,042 A | 12/2000 | Hartley et al. |
| 6,168,568 B1 * | 1/2001 | Gavriely .................. 600/529 |
| 6,181,961 B1 | 1/2001 | Prass |
| 6,190,326 B1 | 2/2001 | McKinnon et al. |
| 6,200,265 B1 | 3/2001 | Walsh et al. |
| 6,212,435 B1 | 4/2001 | Lattner et al. |
| 6,221,011 B1 | 4/2001 | Bardy |
| 6,236,873 B1 | 5/2001 | Holmström |
| 6,240,316 B1 | 5/2001 | Richmond et al. |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,261,238 B1 | 7/2001 | Gavriely |
| 6,263,244 B1 | 7/2001 | Mann et al. |
| 6,264,606 B1 | 7/2001 | Ekwall et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,286,508 B1 | 9/2001 | Remmers et al. |
| 6,287,264 B1 | 9/2001 | Hoffman |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Hartley et al. |
| 6,351,670 B1 | 2/2002 | Kroll |

| Patent | Date | Inventor |
|---|---|---|
| 6,353,759 B1 | 3/2002 | Hartley et al. |
| 6,357,444 B1 | 3/2002 | Parker |
| 6,358,203 B2 | 3/2002 | Bardy |
| 6,361,494 B1 | 3/2002 | Lindenthaler |
| 6,361,522 B1 | 3/2002 | Scheiner et al. |
| 6,363,270 B1 | 3/2002 | Colla et al. |
| 6,366,813 B1 | 4/2002 | DiLorenzo |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,375,623 B1 | 4/2002 | Gavriely |
| 6,387,907 B1 | 5/2002 | Hendricks et al. |
| 6,397,845 B1 | 6/2002 | Burton |
| 6,398,728 B1 | 6/2002 | Bardy |
| 6,398,739 B1 | 6/2002 | Sullivan et al. |
| 6,409,675 B1 | 6/2002 | Turcott |
| 6,409,676 B2 | 6/2002 | Ruton et al. |
| 6,411,848 B2 | 6/2002 | Kramer et al. |
| 6,411,850 B1 | 6/2002 | Kay et al. |
| 6,414,183 B1 | 7/2002 | Sakamoto et al. |
| 6,415,183 B1 | 7/2002 | Scheiner et al. |
| 6,424,865 B1 | 7/2002 | Ding |
| 6,431,171 B1 | 8/2002 | Burton |
| 6,438,407 B1 | 8/2002 | Ousdigian et al. |
| 6,438,410 B2 | 8/2002 | Hsu et al. |
| 6,440,066 B1 | 8/2002 | Bardy |
| 6,442,413 B1 | 8/2002 | Silver |
| 6,447,459 B1 * | 9/2002 | Larom ................ 600/538 |
| 6,449,503 B1 | 9/2002 | Hsu |
| 6,454,719 B1 | 9/2002 | Greenhut |
| 6,459,929 B1 | 10/2002 | Hopper et al. |
| 6,463,326 B1 | 10/2002 | Hartley et al. |
| 6,467,333 B2 * | 10/2002 | Lewis et al. ............ 73/31.05 |
| 6,468,219 B1 | 10/2002 | Njemanze |
| 6,480,733 B1 | 11/2002 | Turcott |
| 6,487,443 B2 | 11/2002 | Olson et al. |
| 6,497,658 B2 | 12/2002 | Roizen et al. |
| 6,527,729 B1 | 3/2003 | Turcott |
| 6,542,775 B2 | 4/2003 | Ding et al. |
| 6,547,743 B2 | 4/2003 | Brydon |
| 6,572,543 B1 * | 6/2003 | Christopherson et al. ... 600/300 |
| 6,574,507 B1 | 6/2003 | Bonnet |
| 6,580,944 B1 | 6/2003 | Katz et al. |
| 6,589,188 B1 | 7/2003 | Street et al. |
| 6,595,928 B2 * | 7/2003 | Mansy et al. ............. 600/529 |
| 6,597,951 B2 | 7/2003 | Kramer et al. |
| 6,600,949 B1 | 7/2003 | Turcott |
| 6,606,993 B1 | 8/2003 | Wiesmann et al. |
| 6,641,542 B2 | 11/2003 | Cho et al. |
| 6,658,292 B2 | 12/2003 | Kroll et al. |
| 6,662,032 B1 * | 12/2003 | Gavish et al. ............. 600/323 |
| 6,679,250 B2 * | 1/2004 | Walker et al. .......... 128/200.21 |
| 6,694,186 B2 | 2/2004 | Bardy |
| 6,723,055 B2 | 4/2004 | Hoffman |
| 6,731,984 B2 | 5/2004 | Cho et al. |
| 6,741,885 B1 | 5/2004 | Park et al. |
| 6,748,252 B2 * | 6/2004 | Lynn et al. .................. 600/323 |
| 6,752,765 B1 | 6/2004 | Jensen et al. |
| 6,752,766 B2 | 6/2004 | Kowallik et al. |
| 6,765,062 B2 | 7/2004 | Chin et al. |
| 6,770,022 B2 | 8/2004 | Mechlenburg et al. |
| 6,770,029 B2 * | 8/2004 | Iliff ........................ 600/300 |
| 6,773,404 B2 | 8/2004 | Poezevara et al. |
| 6,786,866 B2 | 9/2004 | Odagiri et al. |
| 6,810,287 B2 | 10/2004 | Zhu et al. |
| 6,830,548 B2 | 12/2004 | Bonnet et al. |
| 6,881,192 B1 | 4/2005 | Park |
| 6,895,275 B2 | 5/2005 | Markowitz et al. |
| 6,904,320 B2 | 6/2005 | Park et al. |
| 6,910,481 B2 * | 6/2005 | Kimmel et al. ........ 128/204.23 |
| 6,912,419 B2 | 6/2005 | Hill et al. |
| 6,928,324 B2 | 8/2005 | Park et al. |
| 6,932,084 B2 | 8/2005 | Estes et al. |
| 6,951,539 B2 | 10/2005 | Bardy |
| 6,964,641 B2 | 11/2005 | Cho et al. |
| 6,988,498 B2 | 1/2006 | Berthon-Jones et al. |
| 6,999,817 B2 | 2/2006 | Park et al. |
| 7,025,730 B2 | 4/2006 | Cho et al. |
| 7,027,871 B2 | 4/2006 | Burnes et al. |
| 7,062,308 B1 | 6/2006 | Jackson |
| 7,065,409 B2 | 6/2006 | Mazar |
| 7,089,936 B2 | 8/2006 | Madaus et al. |
| 7,092,755 B2 | 8/2006 | Florio |
| 7,117,036 B2 | 10/2006 | Florio |
| 7,127,290 B2 | 10/2006 | Girouard et al. |
| 7,127,300 B2 | 10/2006 | Mazar et al. |
| 7,130,687 B2 | 10/2006 | Cho et al. |
| 7,136,704 B2 | 11/2006 | Schulman |
| 7,155,278 B2 | 12/2006 | King et al. |
| 7,160,252 B2 | 1/2007 | Cho et al. |
| 7,184,817 B2 | 2/2007 | Zhu et al. |
| 7,189,204 B2 | 3/2007 | Ni et al. |
| 7,206,635 B2 | 4/2007 | Cho et al. |
| 7,207,945 B2 | 4/2007 | Bardy |
| 7,212,862 B2 | 5/2007 | Park et al. |
| 7,225,013 B2 | 5/2007 | Geva et al. |
| 7,225,021 B1 | 5/2007 | Park et al. |
| 7,225,809 B1 | 6/2007 | Bowen et al. |
| 7,231,250 B2 | 6/2007 | Band et al. |
| 7,245,971 B2 | 7/2007 | Park et al. |
| 7,252,640 B2 | 8/2007 | Ni et al. |
| 7,269,459 B1 | 9/2007 | Koh |
| 7,302,295 B2 | 11/2007 | Stahmann et al. |
| 7,308,311 B2 | 12/2007 | Sorensen et al. |
| 7,314,046 B2 | 1/2008 | Schroeder et al. |
| 7,376,463 B2 | 5/2008 | Salo et al. |
| 7,396,333 B2 | 7/2008 | Stahmann et al. |
| 7,400,928 B2 | 7/2008 | Hatlestad |
| 7,413,549 B1 * | 8/2008 | Koh ........................ 600/529 |
| 7,428,468 B2 | 9/2008 | Takemura et al. |
| 7,438,686 B2 | 10/2008 | Cho et al. |
| 7,440,795 B2 | 10/2008 | Poezevara |
| 2002/0120207 A1 * | 8/2002 | Hoffman ................. 600/538 |
| 2002/0193685 A1 | 12/2002 | Mate et al. |
| 2003/0023184 A1 | 1/2003 | Pitts-Crick et al. |
| 2003/0050538 A1 | 3/2003 | Naghavi et al. |
| 2003/0055461 A1 | 3/2003 | Girouard et al. |
| 2003/0073919 A1 * | 4/2003 | Hampton et al. ............. 600/532 |
| 2003/0083241 A1 | 5/2003 | Young |
| 2003/0100925 A1 | 5/2003 | Pape et al. |
| 2003/0163059 A1 | 8/2003 | Poezevara et al. |
| 2003/0171687 A1 * | 9/2003 | Irie et al. .................... 600/532 |
| 2003/0178031 A1 | 9/2003 | Du Pen et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0216789 A1 | 11/2003 | Deem et al. |
| 2004/0059240 A1 | 3/2004 | Cho et al. |
| 2004/0073093 A1 | 4/2004 | Hatlestad |
| 2004/0088027 A1 | 5/2004 | Burnes et al. |
| 2004/0128161 A1 | 7/2004 | Mazar et al. |
| 2004/0133079 A1 | 7/2004 | Mazar et al. |
| 2004/0138719 A1 | 7/2004 | Cho et al. |
| 2004/0163648 A1 | 8/2004 | Burton |
| 2004/0210154 A1 * | 10/2004 | Kline ....................... 600/532 |
| 2005/0039745 A1 | 2/2005 | Stahmann et al. |
| 2005/0042589 A1 | 2/2005 | Hatlestad et al. |
| 2005/0043652 A1 | 2/2005 | Lovett et al. |
| 2005/0043772 A1 | 2/2005 | Stahmann et al. |
| 2005/0061315 A1 | 3/2005 | Lee et al. |
| 2005/0065447 A1 | 3/2005 | Lee et al. |
| 2005/0065572 A1 | 3/2005 | Hartley et al. |
| 2005/0085865 A1 | 4/2005 | Tehrani |
| 2005/0101841 A9 | 5/2005 | Kaylor et al. |
| 2005/0107838 A1 | 5/2005 | Lovett et al. |

| | | | |
|---|---|---|---|
| 2005/0142070 A1* | 6/2005 | Hartley et al. ............... | 424/45 |
| 2005/0145246 A1 | 7/2005 | Hartley et al. | |
| 2005/0159784 A1 | 7/2005 | Arceta | |
| 2006/0142645 A1* | 6/2006 | Rice ........................ | 600/300 |
| 2006/0178569 A1* | 8/2006 | Dean ........................ | 600/300 |
| 2006/0293714 A1 | 12/2006 | Salo et al. | |
| 2007/0055115 A1* | 3/2007 | Kwok et al. ............... | 600/300 |
| 2007/0112388 A1 | 5/2007 | Salo | |
| 2007/0149860 A1* | 6/2007 | Lynn et al. ................ | 600/300 |
| 2007/0150014 A1 | 6/2007 | Kramer et al. | |
| 2007/0161873 A1 | 7/2007 | Ni et al. | |
| 2007/0282215 A1 | 12/2007 | Ni et al. | |
| 2008/0045813 A1* | 2/2008 | Phuah et al. ............... | 600/301 |
| 2009/0007918 A1* | 1/2009 | Darkin et al. .......... | 128/205.25 |

FOREIGN PATENT DOCUMENTS

| | | |
|---|---|---|
| EP | 0770407 | 5/1997 |
| EP | 0 940 155 A | 9/1999 |
| EP | 0940155 | 9/1999 |
| EP | 1151718 | 11/2001 |
| EP | 1162125 | 12/2001 |
| EP | 1172125 | 1/2002 |
| EP | 1317943 | 6/2003 |
| WO | WO8402080 | 7/1984 |
| WO | WO9203983 | 3/1992 |
| WO | 99/04841 | 2/1999 |
| WO | WO0001438 | 1/2000 |
| WO | WO 00/17615 | 3/2000 |
| WO | WO00017615 | 3/2000 |
| WO | 02/087696 | 11/2002 |
| WO | WO03075744 | 9/2003 |
| WO | WO2004062485 | 7/2004 |
| WO | WO2005028029 | 3/2005 |

OTHER PUBLICATIONS

Reddel et al., *Analysis of Adherence to Peak Flow Monitoring When Recording of Data is Electronic*, BMJ 146-147 (2002).
Aircraft Noise and Sleep Disturbance final report http /www.caa.co.uk/docs/33/ERCD%208008, 1980.
Altshule et al., *The Effect of Position on Periodic Breathing in Chronic Cardiac Decomposition*, New Eng. Journal of Med., vol. 259, No. 22, pp. 1064-1066 (Nov. 27, 1958). No Copy.
Balaban et al., *Feasibility of Screening for Sleep Apnea Using Pacemaker Impedance Sensor*, NASPE (2001).
Bradley et al, *Cardiac Output Response To Continuous Positive Airway Pressure In Congestive Heart Failure*, 145 Am. Rev. Respir. Dis. 377-382 (1992). (Abstract only).
Bradley et al., Pathophysiologic and Therapeutic Implications of Sleep Apnea in Congestive Heart Failure, 3 J. Cardiac Failure 223-240 (1996). Abstract only.
Bradley et al., *Sleep Apnea and Heart Failure, Park I: Obstructive Sleep Apnea*, 107 Circulation 1671-1678 (2003).
Buda et al., *Effect Of Intrathoracic Pressure On Left Ventricular Performance*, 301 Engl. J. Med. 453-459 (1979). (Abstract only).
Calvin et al., *Positive End-Expiratory Pressure (PEEP) Does Not Depress Left Ventricular Function In Patients With Pulmonary Edema*, 124 Am. Rev. Respir. Dis. 121-128 (1981). (Abstract only).
Dark et al., *Breathing Pattern Abnormalities and Arterial Oxygen Desaturation During Sleep in the Congestive Heart Failure Syndrome*, Chest, 6:833-6 (Jun. 1987).
De Hoyos et al., *Haemodynamic Effects Of Continuous Positive Airway Pressure In Humans With Normal And Impaired Left Ventricular Function*, 88 Clin. Sci. (Lond). 173-8 (1995). (Abstract only).
Garrigue et al., Benefit of Atrial Pacing in Sleep Apnea Syndrome, 346 N. Engl. J. Med. 404-412 (2002). Abstract only.
Garrigue et al., Night Atrial Overdrive with DDD Pacing Results in a Significant Reduction of Sleep Apnea Episodes and QOL Improvement in Heart Failure Patients, NASPE (2001).
Giardino et al., *Respiratory Sinus Arrhythmia is Associated with the Efficiency of Pulmonary Gas Exchange in Healthy Humans*, 284 Am. J. Physiol. H1585-1591 (2003).
Hanson et al., *Cardiac Gated Ventilation*, 2433 SPIE 303-308 (1995).

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999). Abstract only.
Hoffman et al., Cheyne-Stokes Respiration in Patients Recovering from Acute Cardiogenic Pulmonary Edema, Chest, 97:410-12 (1990).
Javaheri et al., Sleep Apnea in 81 Ambulatory Male Patients with Stable Heart Failure: Types and Their Prevalences, Consequences, and Presentations, 97 Circulation 2154-2159 (1998).
Junyu et al., *Posture Detection Algorithm Using Multi Axis DC-Accelerometer*, Pace vol. 22 (Apr. 1999). No Copy.
Kaye et al., *Acute Effects Of Continuous Positive Airway Pressure On Cardiac Sympathetic Tone In Congestive Heart Failure*, 103 Circulation 2336-2338 (2001).
Laude et al., *Effects of Breathing Pattern on Blood Pressure and Heart Rate Oscillations in Humans*, 20 Clin. Exp. Pharmol. Phisiol 619, 625 (1993). Abstract only.
Lenique et al., *Ventilatory And Hemodynamic Effects Of Continuous Positive Airway Pressure In Left Heart Failure*, 155 Am. J. Respir. Crit. Care Med. 500-505 (1997). (Abstract only).
Mehta et al., *Effects Of Continuous Positive Airway Pressure On Cardiac Volumes In Patients With Ischemic And Dilated Cardiomyopathy*, 161 Am. J. Respir. Crit. Care Med. 128-134 (2000).
Naughton et al., *Effects Of Continuous Positive Airway Pressure On Intrathoracic And Left Ventricular Transmural Pressure In Congestive Heart Failure*, 91 Circulation 1725-1731 (1995).
Office Action dated Jun. 29, 2007 from co-pending U.S. Appl. No. 10/643,016, filed Aug. 18, 2003.
Olusola et al., Nightcap: Laboratory and home-based evaluation of a portable sleep monitor, 32 Psychophysiology, 32-98 (1995). Abstract only.
Pinsky et al., *Hemodynamic Effect Of Cardiac Cycle-Specific Increases In Intrathoracic Pressure*, 6 J. Appl. Physiol. 604-612 (1986).
Potkin et al., *Effect of positive end-expiratory pressure on right and left ventricular function in patients with the adult respiratory distress syndrome*, 135 Am. Rev. Respir. Dis. 307-311 (1987). (Abstract only).
Rees et al., Paroxysmal Nocturnal Dyspnoea and Periodic Respiration, The Lancet, Dec. 22-29, 1979, pp. 1315-1317. Abstract only.
Roche et al., Screening of Obstructive Sleep Apnea Syndrome by Heart Rate Variability Analysis, 100 Circulation 1411-1455 (1999).
Scharf, *Effects Of Continuous Positive Airway Pressure On Cardiac Output In Experimental Heart Failure*, 19 Sleep S240-2 (1996). (Abstract only).
Shahrokh, A Mechanism of Central Sleep Apnea In Patients With Heart Failure, 341 N. Engl. J. Med. 949-954 (1999). Abstract only.
Steltner et al., *Diagnosis of Sleep Apena by Automatic Analysis of Nasal Pressure and Forced Oscillation Impedance*. Am. Journal Respiratory Critical Care Medicine, vol. 165, pp. 940-944 (2002).
Tkacova et al., *Left Ventricular Volume in Patients with Heart Failure and Cheyne-Strokes Respiration during Sleep*, Am. Journal, Respir. Crit. Care Med., vol. 156, pp. 1549-1555 (1997).
Vanninen et al., Cardiac Sympathovagal Balance During Sleep Apnea Episodes, 16 Clin. Physiol. 209-216 (1996). Abstract only.
Verrier et al., Sleep, dreams, and sudden death: the case for sleep as an autonomic stress test for the heart, 31 Cardiovascular Research 181-211 (1996).
Verrier et al., Sleep Related Cardiovascular Risk: New Home-Based Monitoring Technology for Improved Diagnosis and Therapy, 2 A.N. E. 158-175 (1997).
Waldemark et al., Detection of Apnea using Short Window FFT Technique and Artificial Neural Network, 3390 SPIE International Society for Optical Engineering 122-133 (1998).
Weber et al. *Effect of CPAP and BIPAP on stroke volume in patients with obstructive sleep apnea syndrome*. Pneumolgie; 49(3):233-5. (1995) (Abstract only).
Young et al., The Occurrence of Sleep-Disordered Breathing Among Middle Aged Adults, N. Engl. J. Med. 1230-1235 (1993). Abstract only.

* cited by examiner

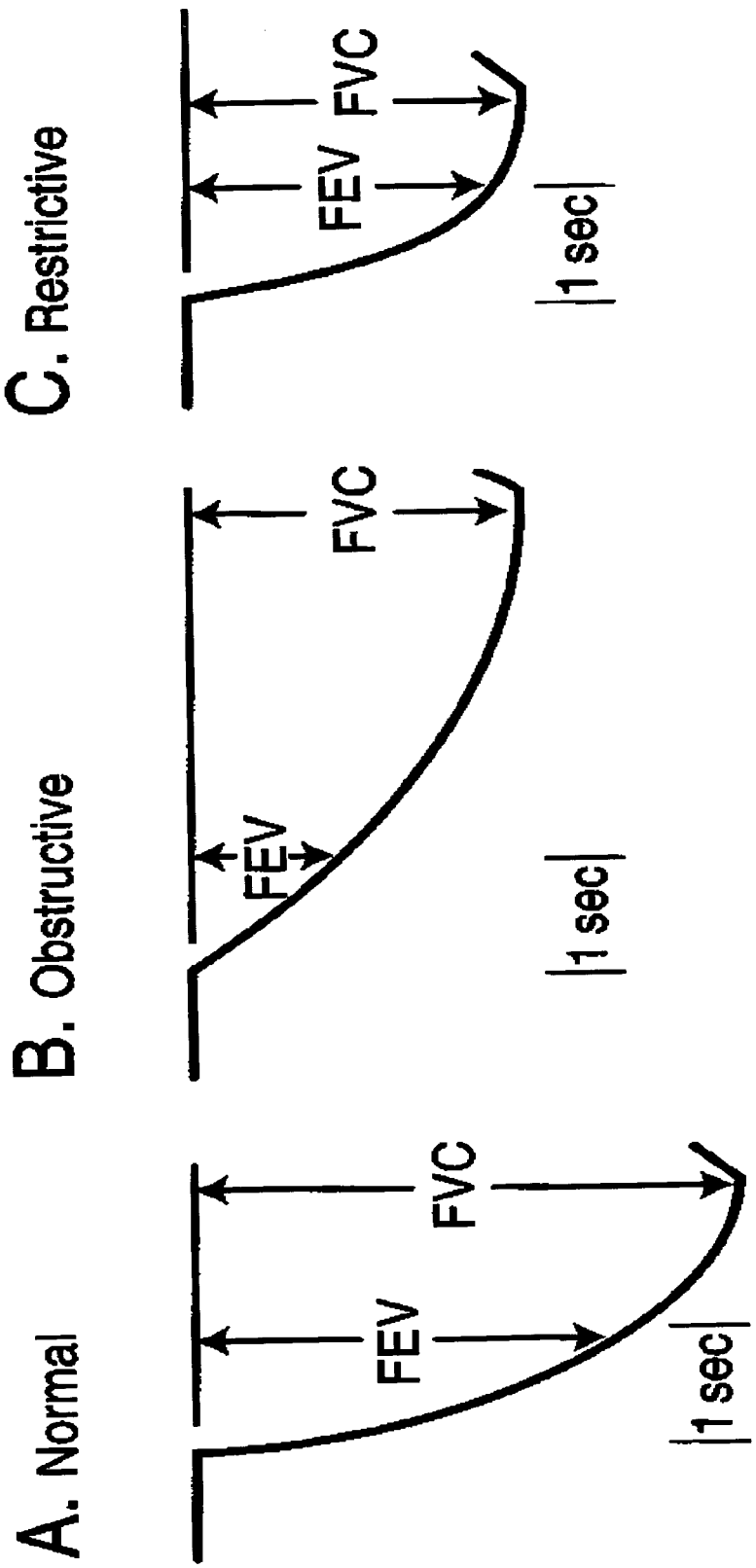

DETECTION OF PULMONARY DISEASES/DISORDERS
Conditions and Sensors

| Sensors | | |
|---|---|---|
| CRM Sensors | | x (Right Ventricular Egram, Left Ventricular Egram, RA Egram, LA Egram, Accelerometer) |
| CPAP Sensors | | |
| External Non-CPAP/CRM | | x |

Sensor columns (601):
- Right Ventricular Egram: RV R-wave Temporal Location, RV R-wave Morphology, RV R-wave Amplitude, RV T-wave Morphology, RV T-wave Temporal Location, RV QT Segment Elevation
- Left Ventricular Egram: LV R-wave Morphology, LV R-wave Amplitude, LV R-wave Temporal Location, LV T-wave Morphology, LV T-wave Temporal Location, LV QT Segment Elevation
- RA Egram: RA P-wave Morphology, RA P-wave Amplitude, RA P-wave Temporal Location
- LA Egram: RA P-wave Morphology, RA P-wave Amplitude, RA P-wave Temporal Location
- Accelerometer: Activity, Heart Sounds, Respiration Sounds, Posture (610-1)

Physiological Changes (604):

| Physiological Changes | Notable Sensor Entries (x marks) |
|---|---|
| Dyspnea | |
| Non-specific Dyspnea | Posture (x) |
| Orthopnea | Posture (x) |
| Exertional Dyspnea | |
| Paroxysmal Nocturnal Dyspnea | Posture (x) |
| Blood / Respiratory Gases | |
| Cyanosis | |
| Hypoxemia | LV R-wave Morphology (x), RA P-wave Amplitude (x), RA P-wave Morphology (LA) (x) |
| Hypercapnea | LV R-wave Amplitude (x), RA P-wave Morphology (RA) (x), RA P-wave Amplitude (LA) (x) |
| Low pCO2 | |
| Arterial acidosis | |
| High Alveolar-Arterial pO2 Diff | |
| Respiratory Sounds | |
| Wheezing | Respiration Sounds (x), Posture (x) |
| Crackles | Respiration Sounds (x), Posture (x) |
| Rhonchi | Respiration Sounds (x), Posture (x) |
| Fiction Rub | Heart Sounds (x), Respiration Sounds (x), Posture (x) |
| Attenuated Breath Sounds | Respiration Sounds (x), Posture (x) |
| Snoring | Respiration Sounds (x), Posture (x) |

Fig. 3B-1

DETECTION OF PULMONARY DISEASES/DISORDERS
Conditions and Sensors

| | Transthoracic Impedance | | | | | Heart Motion Morphology | DC Thoracic Impedance | Blood Pressure | | | | | Blood Gas | | |
|---|---|---|---|---|---|---|---|---|---|---|---|---|---|---|---|
| | Respiration Rate | Tidal Volume | Minute Ventilation | Inspiration Time | Exhalation Time | | | Systolic Blood Pressure | Diastolic Blood Pressure | Pulse Pressure | Wedge Pressure | Contractility (dP/dt) | Blood pO2 | Blood pCO2 | Arterial/Venous pO2 |
| CRM Sensors | x | | | | | | | x | | | | | x | | |
| CPAP Sensors | | | | | | | | | | | | | | | |
| External Non-CPAP/CRM | x | | | | | | | x | | | | | x | | |

Physiological Changes

| | Respiration Rate | Tidal Volume | Minute Ventilation | Inspiration Time | Exhalation Time | Heart Motion Morphology | DC Thoracic Impedance | Systolic Blood Pressure | Diastolic Blood Pressure | Pulse Pressure | Wedge Pressure | Contractility (dP/dt) | Blood pO2 | Blood pCO2 | Arterial/Venous pO2 |
|---|---|---|---|---|---|---|---|---|---|---|---|---|---|---|---|
| Pulmonary Function | | | | | | | | | | | | | | | |
| Low FEV, FVC, FEV/FVC | | | | x | x | | | | | | | | | | |
| Low FEF | | | | x | x | | | | | | | | | | |
| High FRC, TLC | | | | x | x | | | | | | | | | | |
| High RV | | | | x | x | | | | | | | | | | |
| High Lung Compliance | | | | | x | | | | | | | | | | |
| Slow Exhalation | | | | | x | | | | | | | | | | |
| Tachypnea | x | | | | | | | | | | | | | | |
| Shallow (Low Tidal Volume) Breathing | | x | x | | | | | | | | | | | | |
| High Minute Ventilation | x | x | x | | | | | | | | | | | | |
| Respiratory Failure | x | x | x | | | | | | | | | x | x | x | x |
| Reduced Diffusion Capacity | | | | | | | | | | | | | x | x | x |

Fig. 3D-1 — DETECTION OF PULMONARY DISEASES/DISORDERS — Conditions and Sensors Sensor groups (601): CRM Sensors, CPAP Sensors, External Non-CPAP/CRM

| Sensor category | Sub-sensors | CRM | CPAP | Ext. Non-CPAP/CRM |
|---|---|---|---|---|
| Right Ventricular Egram | RV R-wave Temporal Location, RV R-wave Morphology, RV R-wave Amplitude, RV T-wave Temporal Location, RV T-wave Morphology, RV QT Segment Elevation | X | | X |
| Left Ventricular Egram | LV R-wave Temporal Location, LV R-wave Morphology, LV R-wave Amplitude, LV T-wave Temporal Location, LV T-wave Morphology, LV QT Segment Elevation | X | | X |
| RA Egram | RA P-wave Temporal Location, RA P-wave Morphology, RA P-wave Amplitude | X | | X |
| LA Egram | RA P-wave Temporal Location, RA P-wave Morphology, RA P-wave Amplitude | X | | X |
| Accelerometer (614-1) | Activity, Heart Sounds, Respiration Sounds, Posture | X | | X |

Physiological Changes (604) — Other Pulmonary:

| Physiological Change | LV R-wave Amplitude | LV QT Segment Elevation | RA P-wave Temporal Location | Posture |
|---|---|---|---|---|
| Hemoptysis | | | | |
| Cough | | | | X |
| Pleuritic Chest Pain | X | X | X | X |
| Local Inflammation | X | | | |
| Excess Mucous Production | | | | |
| Chest Pain | X | X | X | |
| Respiratory Infection (sligt. elev. WBC) | | | | |
| Pulmonary Mucus | | | | |
| Overinfl. Lungs->barrel-shaped chest | | | | |
| Alveolar wall breakdown | | | | |
| Mucosal Pulmonary Edema | | | | |
| Ventilation-perfusion mismatch | | | | |
| Subepithelial Fibrosis (chronically) | | | | |
| Respiratory Muscle Fatigue | | | | X |
| High small airway resistance | | | | |
| Hoarseness | | | | |

DETECTION OF PULMONARY DISEASES/DISORDERS
Conditions and Sensors

| | CRM Sensors | | | | | | | | | | | | | | | CPAP Sensors | | | External Non-CRM/CPAP | | | |
|---|---|---|---|---|---|---|---|---|---|---|---|---|---|---|---|---|---|---|---|---|---|---|
| | Right Ventricular Egram | | | | | | Left Ventricular Egram | | | | | | RA Egram | | | LA Egram | | | Accelerometer | | | |
| Physiological Changes | RV R-wave Temporal Location | RV R-wave Morphology | RV R-wave Amplitude | RV T-wave Temporal Location | RV T-wave Morphology | RV QT Segment Elevation | LV R-wave Temporal Location | LV R-wave Morphology | LV R-wave Amplitude | LV T-wave Temporal Location | LV T-wave Morphology | LV QT Segment Elevation | RA P-wave Temporal Location | RA P-wave Morphology | RA P-wave Amplitude | RA P-wave Temporal Location | RA P-wave Morphology | RA P-wave Amplitude | Activity | Heart Sounds | Respiration Sounds | Posture |
| Cardiovascular | | | | | | | | | | | | | | | | | | | | | | |
| Pulmonary Hypertension | | | | | | | | | | | | | | | | | | | | | | |
| High Pulmonary Vascular Resistance | | | | | | | | | | | | | | | | | | | | | | |
| Tachycardia | X | | | | | | | | | | | | | | | | | | | | | |
| Circulatory Collapse | | | | | | | | | | | | | | | | | | | | | | |
| Pulsus Paradoxicus | | | | | | | | | | | | | | | | | | | | | | |
| Syncope | | | | | | | | | | | | | | | | | | | | | | |
| Hypertension | | | | | | | | X | | | | | | | | | | | | | | |
| S3 Heart Sound | | | | | | | | | | | | | | | | | | | | X | | |
| Split S2 Heart Sound | | | | | | | | | | | | | | | | | | | | X | | |
| RV Hypertrophy | | | | | X | | | | | | | | | | | | | | | | | |
| Systolic Murmur | | | | | | | | | | | | | | | | | | | | X | | |
| General Systemic | | | | | | | | | | | | | | | | | | | | | | |
| Fever | | | | | | | | | | | | | | | | | | | | | | |
| Weight Loss | | | | | | | | | | | | | | | | | | | | | | |
| Weight Gain | | | | | | | | | | | | | | | | | | | | | | |
| Night Sweats | | | | | | | | | | | | | | | | | | | | | | |
| Peripheral Edema | | | | | | | | | | | | | | | | | | | | | | |
| High Hemoglobin | | | | | | | | | | | | | | | | | | | | | | |
| Fatigue | | | | | | | | | | | | | | | | | | | X | | | |
| Joint Pain | | | | | | | | | | | | | | | | | | | X | | | |
| Hypersomnolence | | | | | | | | | | | | | | | | | | | X | | | |

Fig. 3D-2

DETECTION OF PULMONARY DISEASES/DISORDERS
Conditions and Sensors

| | Transthoracic Impedance | | | | | | | Blood Pressure | | | | | Blood Gas | | |
|---|---|---|---|---|---|---|---|---|---|---|---|---|---|---|---|
| | Respiration Rate | Tidal Volume | Minute Ventilation | Inspiration Time | Exhalation Time | Heart Motion Morphology | DC Thoracic Impedance | Systolic Blood Pressure | Diastolic Blood Pressure | Pulse Pressure | Wedge Pressure | Contractility (dP/dt) | Blood pO2 | Blood pCO2 | Arterial/Venous pO2 |
| CRM Sensors | x | | | | | | | | | | | | | | |
| CPAP Sensors | x | | | | | | | | | | | | | | |
| External Non-CPAP/CRM | | | | | | | | x | | | | | x | | |

Physiological Changes

Other Pulmonary

| | Respiration Rate | Tidal Volume | Minute Ventilation | Inspiration Time | Exhalation Time | Heart Motion Morphology | DC Thoracic Impedance | Systolic BP | Diastolic BP | Pulse Pressure | Wedge Pressure | Contractility | Blood pO2 | Blood pCO2 | Arterial/Venous pO2 |
|---|---|---|---|---|---|---|---|---|---|---|---|---|---|---|---|
| Hemoptysis | | | | | | | | | | | | | | | |
| Cough | | | X | | | | | | | | | | | | |
| Pleuritic Chest Pain | | X | X | | | | | | | | | | | | |
| Local Inflammation | | | | | | | | | | | | | | | |
| Excess Mucous Production | | X | X | X | X | | | | | | | | | | |
| Chest Pain | | X | | | | | | | | | | | | | |
| Respiratory Infection (slight elev. WBC) | | | | | | | | | | | | | | | |
| Pulmonary Mucus | | X | X | X | X | | | | | | | | | | |
| Overinflat. Lungs→barrel-shaped chest | | X | X | X | X | | | | X | | | | | | |
| Alveolar wall breakdown | | | | | | | | | | | | | | | |
| Mucosal Pulmonary Edema | | X | X | X | X | | | | X | | | | | | |
| Ventilation-perfusion mismatch | | | | | | | | | | | | | | X | X |
| Subepithelial Fibrosis (chronically) | | | | | | | | | | | | | | | |
| Respiratory Muscle Fatigue | | X | X | X | | | | | | | | | | X | X |
| High small airway resistance | | X | X | X | X | | | | | | | | | | |
| Hoarseness | | | | | | | | | | | | | | | |

DETECTION OF PULMONARY DISEASES/DISORDERS

Pulmonary Diseases/Disorders (620-2):

| Physiological Changes (604) | COPD – Obstructive | | | Restrictive | | | | | | | Infectious | | Pul Vasculature | | | Pleural | | | Rhythm | | | | Other | |
|---|---|---|---|---|---|---|---|---|---|---|---|---|---|---|---|---|---|---|---|---|---|---|---|---|
| | Chronic Bronchitis | Emphysema | Asthma | Sarcoidosis | Pulmonary Fibrosis | Pneumoconiosis | Bronchitis | Pneumonia | Bronchiolitis | Tuberculosis | Bronchiectasis | Pulmonary Hypertension | Pulmonary Edema | Atelectasis | Pulmonary Embolism | Pleural Effusion | Pneumothorax | Hemothorax | Apnea (obstructive & central) | Hypopnea (obstructive & central) | Cheyne-Stokes | Periodic Breathing | Lung Cancer | ARDS |
| Pulmonary Function | | | | | | | | | | | | | | | | | | | | | | | | |
| Low FEV, FVC, FEV/FVC | X | X | | | | | | | | | | | | | | | | | | | | | | |
| Low FEF | X | X | | | | | | | | | | | | | | | | | | | | | | |
| High FRC, TLC | X | X | | | | | | | | | | | | | | | | | | | | | | |
| High RV | | X | | | | | | | | | | | | | | | | | | | | | | |
| High Lung Compliance | X | X | | | | | | | | | | | | | | | | | | | | | | |
| Slow Exhalation | X | X | | | | | | | | | | | | | | | | | | | | | | |
| Tachypnea | X | | | X | | | | X | | | X | | | | | | | | | | | | | |
| Shallow (Low Tidal Volume) Breathing | X | | | X | | | | X | | | X | | | | | | | | | | | | | |
| High Minute Ventilation | X | | | | | | | | | | | | | | | | | | | | | | | |
| Respiratory Failure | X | | | X | | | | | | | | | | | X | | | | | | | | | |
| Reduced Diffusion Capacity | | | | | | | | | | | | | | | | | | | | | | | | |

Fig. 3G-1 — DETECTION OF PULMONARY DISEASES/DISORDERS

Pulmonary Diseases/Disorders (columns) grouped as:
- Obstructive (COPD): Chronic Bronchitis, Emphysema, Asthma
- Restrictive: Sarcoidosis, Pulmonary Fibrosis, Pneumoconiosis, Bronchitis, Pneumonia, Bronchiolitis
- Infectious: Tuberculosis, Bronchiectasis
- Pul Vasculature: Pulmonary Hypertension, Pulmonary Edema, Atelectasis
- Pleural: Pleural Effusion, Pneumothorax, Hemothorax
- Rhythm: Apnea (obstructive & central), Hypopnea (obstructive & central), Cheyne-Stokes Periodic Breathing
- Other: Lung Cancer, ARDS Physiological Changes (604):

| Physiological Changes | Chr. Bronchitis | Emphysema | Asthma | Sarcoidosis | Pulm. Fibrosis | Pneumoconiosis | Bronchitis | Pneumonia | Bronchiolitis | Tuberculosis | Bronchiectasis | Pulm. Hypertension | Pulm. Edema | Atelectasis | Pleural Effusion | Pneumothorax | Hemothorax | Apnea | Hypopnea | Cheyne-Stokes | Lung Cancer | ARDS |
|---|---|---|---|---|---|---|---|---|---|---|---|---|---|---|---|---|---|---|---|---|---|---|
| Hemoptysis | X |  |  |  |  |  | X | X | X | X | X |  |  |  |  |  |  |  |  |  |  |  |
| Cough | X | X | X | X | X | X | X | X | X | X | X |  |  |  |  |  |  |  |  |  |  |  |
| Pleuritic Chest Pain |  |  |  |  |  |  |  | X |  |  |  |  |  |  |  |  |  |  |  |  |  |  |
| Local Inflammation |  |  |  |  | X |  |  |  |  |  |  |  |  |  |  |  |  |  |  |  |  |  |
| Excess Mucous Production |  |  |  |  | X |  |  |  |  |  |  |  |  |  |  |  |  |  |  |  |  |  |
| Chest Pain | X |  |  |  | X |  |  |  |  |  |  |  |  |  | X | X |  |  |  |  |  |  |
| Respiratory Infection (slight. elev. WBC) | X | X | X |  | X |  | X | X |  | X | X |  | X |  |  |  |  |  |  |  |  |  |
| Pulmonary Mucus | X | X |  |  |  |  |  |  |  |  |  |  |  |  |  |  |  |  |  |  |  |  |
| Overinfl. Lungs→barrel-shaped chest |  | X |  |  |  |  |  |  |  |  |  |  |  |  |  |  |  |  |  |  |  |  |
| Alveolar wall breakdown |  | X |  |  |  |  |  |  |  |  |  |  |  |  |  |  |  |  |  |  |  |  |
| Mucosal Pulmonary Edema | X |  |  |  |  |  |  |  |  |  |  |  |  |  |  |  |  |  |  |  |  |  |
| Ventilation-perfusion mismatch | X | X |  |  |  |  |  |  |  |  |  |  |  |  |  |  |  |  |  |  |  |  |
| Subepithelial Fibrosis (chronically) |  |  |  |  |  |  |  |  |  |  |  |  |  |  |  |  |  |  |  |  |  |  |
| Respiratory Muscle Fatigue | X |  |  |  |  |  |  |  |  |  |  |  |  |  |  |  |  |  |  |  |  |  |
| High small airway resistance |  |  | X |  |  |  |  |  |  |  | X |  |  |  |  |  |  |  |  |  |  |  |
| Hoarseness |  |  |  |  |  |  |  |  |  |  |  |  |  |  |  |  |  |  |  |  |  |  |

622-1

Criteria Set for Assessment of Chronic Bronchitis

| Physiological Change or Symptom Associated with Chronic Bronchitis | Condition Used to Detect the Physiological Change or Symptom | Respiration Therapy Device Sensor Used to Sense Condition |
|---|---|---|
| Non-Specific Dyspnea | Exhaled % $CO_2$ | $CO_2$ Gas Sensor |
|  | Exhaled % $CO_2$ | $O_2$ Gas Sensor |
|  | Expiratory Flow | Expiratory Flowmeter |
|  | Inspiratory Flow | Inspiratory Flowmeter |
| Cyanosis | Exhaled % $O_2$ | $O_2$ Gas Sensor |
| Hypoxemia | Exhaled % $O_2$ | $O_2$ Gas Sensor |
| Hypercapnea | Exhaled % $CO_2$ | $CO_2$ Gas Sensor |
| Low $pCO_2$ | Exhaled % $CO_2$ | $CO_2$ Gas Sensor |
| Arterial Acidosis | Exhaled % $CO_2$ | $CO_2$ Gas Sensor |
| High Aveolar-Arterial $pO_2$ differential | Exhaled % $O_2$ | $O_2$ Gas Sensor |
| Low FEV, FVC, FEV/FVC | Expiratory Flow | Expiratory Flowmeter |
|  | Inspiratory Flow | Inspiratory Flowmeter |
|  | Expiratory Pressure | Expiratory Pressure Sensor |
|  | Inspiratory Pressure | Inspiratory Pressure Sensor |
| High, FRC, TLC | Expiratory Flow | Expiratory Flowmeter |
|  | Inspiratory Flow | Inspiratory Flowmeter |
|  | Expiratory Pressure | Expiratory Pressure Sensor |
|  | Inspiratory Pressure | Inspiratory Pressure Sensor |
| Slow Exhalation | Expiratory Flow | Expiratory Flowmeter |
|  | Inspiratory Flow | Inspiratory Flowmeter |
|  | Expiratory Pressure | Expiratory Pressure Sensor |
|  | Inspiratory Pressure | Inspiratory Pressure Sensor |
| Ventilation-Perfusion Mismatch | Exhaled % $CO_2$ | $CO_2$ Gas Sensor |
|  | Exhaled % $O_2$ | $O_2$ Gas Sensor |

Figure 4B

Criteria Set for Assessment of Emphysema

| Physiological Change or Symptom Associated with Emphysema | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
|  | Exhaled % O2 | O2 Gas Sensor |
|  | Expiratory Flow | Expiratory Flowmeter |
|  | Inspiratory Flow | Inspiratory Flowmeter |
| Exertional Dyspnea | Exhaled % CO2 | CO2 Gas Sensor |
|  | Exhaled % O2 | O2 Gas Sensor |
|  | Expiratory Flow | Expiratory Flowmeter |
|  | Inspiratory Flow | Inspiratory Flowmeter |
| Cyanosis | Exhaled % O2 | O2 Gas Sensor |
| Hypoxemia | Exhaled % O2 | O2 Gas Sensor |
| Hypercapnia | Exhaled % CO2 | CO2 Gas Sensor |
| Arterial Acidosis | Exhaled % CO2 | CO2 Gas Sensor |
| High Aveolar-Arterial pO2 differential | Exhaled % O2 | O2 Gas Sensor |
| Low FEV, FVC, FEV/FVC | Expiratory Flow | Expiratory Flowmeter |
|  | Inspiratory Flow | Inspiratory Flowmeter |
|  | Expiratory Pressure | Expiratory Pressure Sensor |
|  | Inspiratory Pressure | Inspiratory Pressure Sensor |
| High, FRC, TLC | Expiratory Flow | Expiratory Flowmeter |
|  | Inspiratory Flow | Inspiratory Flowmeter |
|  | Expiratory Pressure | Expiratory Pressure Sensor |
|  | Inspiratory Pressure | Inspiratory Pressure Sensor |
| High Lung Compliance | Expiratory Flow | Expiratory Flowmeter |
|  | Inspiratory Flow | Inspiratory Flowmeter |
|  | Expiratory Pressure | Expiratory Pressure Sensor |
|  | Inspiratory Pressure | Inspiratory Pressure Sensor |
| Slow Exhalation | Expiratory Flow | Expiratory Flowmeter |
|  | Inspiratory Flow | Inspiratory Flowmeter |
|  | Expiratory Pressure | Expiratory Pressure Sensor |
|  | Inspiratory Pressure | Inspiratory Pressure Sensor |
| Ventilation-Perfusion Mismatch | Exhaled % CO2 | CO2 Gas Sensor |
|  | Exhaled % O2 | O2 Gas Sensor |

Figure 4C

Criteria Set for Assessment of Asthma

| Physiological Change or Symptom Associated with Asthma | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Orthopnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Paroxysmal Nocturnal Dysnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| High Aveolar-Arterial pO2 differential | Exhaled % O2 | O2 Gas Sensor |
| Low FEV, FVC, FEV/FVC | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Low FEF | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| High RV | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Slow Exhalation | Expiratory Flow | Expiratory Flowmeter |
| | Inspiratory Flow | Inspiratory Flowmeter |
| | Expiratory Pressure | Expiratory Pressure Sensor |
| | Inspiratory Pressure | Inspiratory Pressure Sensor |
| Ventilation-Perfusion Mismatch | Exhaled % CO2 | CO2 Gas Sensor |
| | Exhaled % O2 | O2 Gas Sensor |

Figure 4D

Criteria Set for Assessment of Pulmonary Fibrosis

| Physiological Change or Symptom Associated with Pulmonary Fibrosis | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Exertional Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Cyanosis | Exhaled % O2 | O2 Gas Sensor |
| Hypoxemia | Exhaled % O2 | O2 Gas Sensor |
| Hypercapnia | Exhaled % CO2 | CO2 Gas Sensor |
| Low pCO2 | Exhaled % CO2 | CO2 Gas Sensor |

Figure 4E

Criteria Set for Assessment of Pulmonary Hypertension

| Physiological Change or Symptom Associated with Pulmonary Hypertension | Condition Used to Detect the Physiological Change or Symptom | Respiration Therapy Device Sensor Used to Sense Condition |
|---|---|---|
| Exertional Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Hypoxemia | Exhaled % O2 | O2 Gas Sensor |

Figure 4F

Criteria Set for Assessment of Pulmonary Edema

| Physiological Change or Symptom Associated with Pulmonary Edema | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Orthopnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Exertional Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Paroxysmal Nocturnal Dysnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Cyanosis | Exhaled % O2 | O2 Gas Sensor |
| Hypoxemia | Exhaled % O2 | O2 Gas Sensor |

Figure 4G

Criteria Set for Assessment of Pulmonary Embolism

| Physiological Change or Symptom Associated with Pulmonary Embolism | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Exertional Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Hypoxemia | Exhaled % O2 | O2 Gas Sensor |

Figure 4H

Criteria Set for Assessment of Atelectasis

| Physiological Change or Symptom Associated with Atelectasis | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Hypoxemia | Exhaled % O2 | O2 Gas Sensor |
| Hypercapnia | Exhaled % CO2 | CO2 Gas Sensor |

Figure 4I

Criteria Set for Assessment of Hemothorax

| Physiological Change or Symptom Associated with Hemothorax | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Hypoxemia | Exhaled % O2 | O2 Gas Sensor |
| Hypercapnia | Exhaled % CO2 | CO2 Gas Sensor |
| Respiratory Failure | Exhaled % CO2 | CO2 Gas Sensor |
| | Exhaled % O2 | O2 Gas Sensor |
| Circulatory Collapse | Exhaled % CO2 | CO2 Gas Sensor |
| | Exhaled % O2 | O2 Gas Sensor |

Figure 4J

Criteria Set for Assessment of Tuberculosis

| Physiological Change or Symptom Associated with Hemothorax | Condition Used to Detect the Physiological Change or Symptom | Respiration Therapy Device Sensor Used to Sense Condition |
|---|---|---|
| Non-Specific Dyspnea | Exhaled % CO2 | CO2 Gas Sensor |
| | Exhaled % O2 | O2 Gas Sensor |
| | Expiratory Flow | Expiratory Flowmeter |
| | Inspiratory Flow | Inspiratory Flowmeter |
| Crackles | Duration of Symptoms | Patient Inquiry |
| | Abnormal Breathing/Coughing | Patient Inquiry |
| | Inspiration Time | Transthoracic Impedance |
| | Expiration Time | Transthoracic Impedance |
| | Respiration Sounds | Accelerometer |
| Hemoptysis | Duration of Symptoms | Patient Inquiry |
| | Abnormal Breathing/Coughing | Patient Inquiry |
| Cough | Duration of Symptoms | Patient Inquiry |
| | Abnormal Breathing/Coughing | Patient Inquiry |
| | Tidal Volume | Transthoracic Impedance |
| | Respiration Sounds | Accelerometer |
| Pleuritic Chest Pain | Duration of Symptoms | Patient Inquiry |
| | Pain | Patient Inquiry |
| | Exhalation Time | Transthoracic Impedance |
| | Inspiration Time | Transthoracic Impedance |
| | Minute Ventilation | Transthoracic Impedance |
| | Tidal Volume | Transthoracic Impedance |
| | Respiration Sounds | Accelerometer |
| | LV QT Segment Elevation | Left Ventricular Egram |
| | LV T wave Morphology | Left Ventricular Egram |
| | RV QT Segment Elevation | Right Ventricular Egram |
| | RV T wave Morphology | Right Ventricular Egram |

Figure 4K

METHODS AND SYSTEMS FOR ASSESSING PULMONARY DISEASE

RELATED PATENT DOCUMENTS

This application claims the benefit of Provisional Patent Application Ser. No. 60/504,711, filed on Sep. 18, 2003, to which priority is claimed pursuant to 35 U.S.C. §119(e) and which is hereby incorporated herein by reference.

FIELD OF THE INVENTION

The present invention relates generally to methods and systems for assessing a presence of pulmonary disease.

BACKGROUND OF THE INVENTION

Diseases and disorders of the pulmonary system are among the leading causes of acute and chronic illness in the world. Pulmonary diseases or disorders may be organized into various categories, including, for example, breathing rhythm disorders, obstructive diseases, restrictive diseases, infectious diseases, pulmonary vasculature disorders, pleural cavity disorders, and others. Pulmonary dysfunction may involve symptoms such as apnea, dyspnea, changes in blood or respiratory gases, symptomatic respiratory sounds, e.g., coughing, wheezing, respiratory insufficiency, and/or general degradation of pulmonary function, among other symptoms.

Breathing rhythm disorders involve patterns of interrupted and/or disrupted breathing. Sleep apnea syndrome (SAS) and Cheyne-Stokes respiration (CSR) are examples of breathing rhythm disorders. Breathing rhythm disorders may be caused by an obstructed airway and/or by derangement of the signals from the brain controlling respiration. Disordered breathing rhythm during sleep is particularly prevalent and is associated with excessive daytime sleepiness, systemic hypertension, increased risk of stroke, angina, and myocardial infarction. Breathing rhythm disorders can be particularly serious for patients concurrently suffering from cardiovascular deficiencies.

Obstructive pulmonary diseases can be associated with a decrease in the total volume of exhaled airflow caused by a narrowing or blockage of the airways. Examples of obstructive pulmonary diseases include asthma, emphysema and bronchitis. Chronic obstructive pulmonary disease (COPD) refers to chronic lung diseases that result in blocked airflow in the lungs. Chronic obstructive pulmonary disease may develop over many years, typically from exposure to cigarette smoke, pollution, or other irritants. Over time, the elasticity of the lung tissue is lost, the lung's air sacs may collapse, the lungs may become distended, partially clogged with mucus, and/or lose the ability to expand and contract normally. As the disease progresses, breathing becomes labored, and the patient grows progressively weaker. Many people with COPD concurrently have both emphysema and chronic bronchitis.

Restrictive pulmonary diseases involve a decrease in the total volume of air that the lungs are able to hold. Often the decrease in total lung volume is due to a decrease in the elasticity of the lungs themselves, or may be caused by a limitation in the expansion of the chest wall during inhalation. Restrictive pulmonary disease can be caused by scarring from pneumonia, tuberculosis, or sarcoidosis. A decrease in lung volume may be the result of various neurologic and/or muscular diseases affecting the neural signals and/or muscular strength of the chest wall and lungs. Examples of neurologic and/or muscular diseases that may affect lung volume include poliomyelitis and multiple sclerosis. Lung volume deficiencies may also be related to congenital or acquired deformities of the chest.

Pulmonary dysfunctions can also involve disorders of the pleural cavity and/or pulmonary vasculature. Pulmonary vasculature disorders may include pulmonary hypertension, pulmonary edema, and pulmonary embolism. Disorders of the pleural cavity include conditions such as pleural effusion, pneumothorax, and hemothorax, for example.

Pulmonary diseases may be caused by infectious agents such as viral and/or bacterial agents. Examples of infectious pulmonary diseases include pneumonia, tuberculosis, and bronchiectasis. Non-infectious pulmonary diseases include lung cancer and adult respiratory distress syndrome (ARDS), for example.

Early detection and diagnosis of various types of pulmonary diseases and syndromes improves the likelihood of successful treatment. The onset of some types of pulmonary disorders is very gradual. Early diagnosis may depend on the recognition of subtle changes in respiratory conditions that may not be apparent during yearly or even monthly check-ups. The patient may compensate for decreases in respiratory capacity, further obscuring detection and diagnosis. Methods and systems providing earlier and more accurate assessment of pulmonary diseases and disorders are desirable.

SUMMARY OF THE INVENTION

Embodiments of the invention are directed to methods and systems for assessing a presence of pulmonary disease. One embodiment of the invention involves a method for assessing a presence of a pulmonary disease other than a breathing rhythm disorder. The method includes sensing one or more conditions associated with the non-rhythm pulmonary disease using a respiratory therapy device. The presence of the non-rhythm pulmonary disease is assessed based on the one or more sensed conditions.

According to various aspects of the invention, sensing the one or more sensed conditions may include sensing one or more of respiratory pressure, respiratory flow, and exhaled gas concentration.

The presence of various types of non-rhythm pulmonary diseases may be assessed, including, for example, obstructive pulmonary diseases, restrictive pulmonary diseases, pulmonary vasculature disorders, pleural disorders, and/or other pulmonary diseases or disorders that are not breathing rhythm disorders.

According to another embodiment of the invention, a medical system for assessing a non-rhythm pulmonary disease presence includes a respiratory therapy device having a therapy unit and a sensor system. The therapy unit is configured to deliver respiration therapy to a patient. The sensor system is configured to sense one or more conditions associated with a pulmonary disease other than a breathing rhythm disorder. The system further includes a diagnosis unit coupled to the sensor system. The diagnosis unit is configured to assess a presence of the non-rhythm pulmonary disease based on the one or more sensed conditions.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 1B-1D are graphs of normal, obstructive and restrictive respiratory patterns, respectively, in accordance with embodiments of the invention;

FIGS. 3A-3G is a chart illustrating relationships between pulmonary diseases, symptoms and/or physiological changes caused by the pulmonary diseases, and conditions used to detect the symptoms and/or physiological changes in accordance with embodiments of the invention;

FIGS. 4B-4K are criteria sets for assessing a presence of various non-rhythm pulmonary diseases in accordance with embodiments of the invention.

Figure 1A:
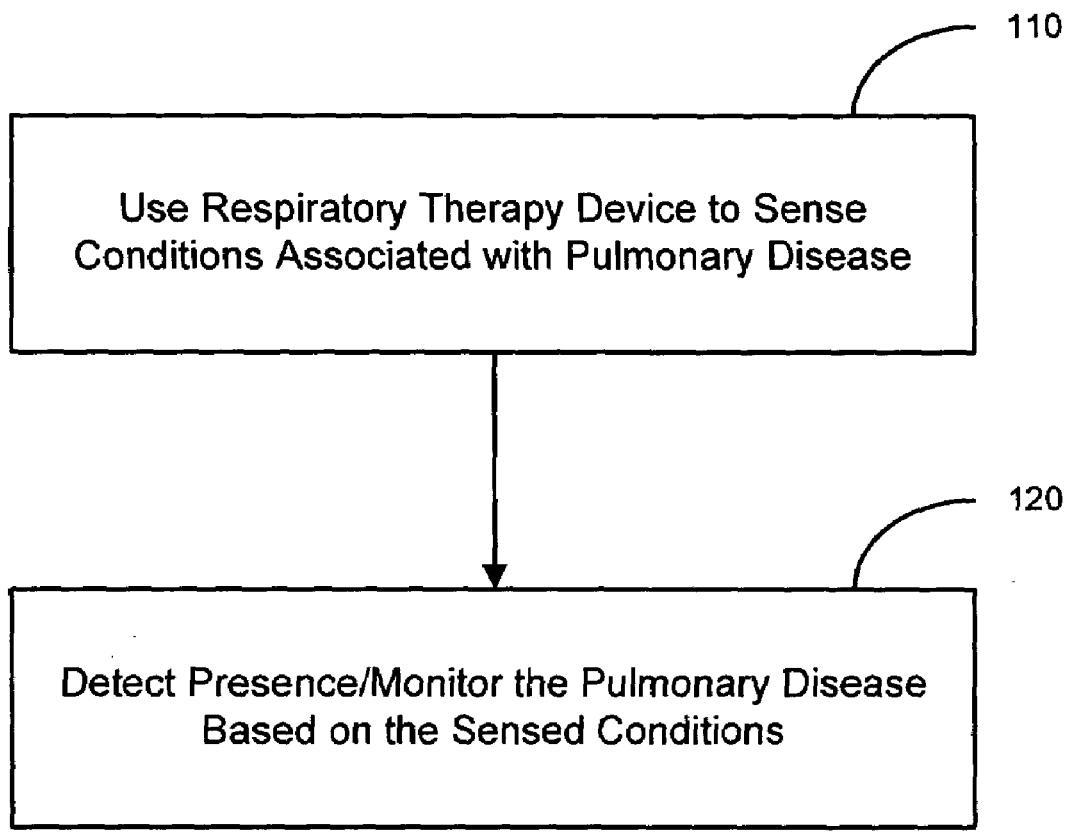
FIG. 1A is a flowchart of a method of diagnosing pulmonary diseases and disorders in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Pulmonary disorders may be organized into broad categories encompassing disorders of breathing rhythm and non-rhythm pulmonary diseases and/or disorders. Breathing rhythm disorders include various syndromes characterized by patterns of disordered breathing that produce insufficient respiration, for example, sleep apnea, hypopnea, and Cheyne-Stokes Respiration (CSR), among others. Breathing rhythm disorders are not necessarily accompanied by alteration of pulmonary structures.

Non-rhythm pulmonary diseases or disorders typically involve physical changes to lung structures, such as loss of elasticity of the lung tissue, obstruction of airways with mucus, limitation of the expansion of the chest wall during inhalation, fibrous tissue within the lung, excessive pressure in the pulmonary arteries, and/or other characteristics. Pulmonary diseases or disorders that are not rhythm-related are referred to herein as non-rhythm pulmonary diseases and may include obstructive pulmonary diseases, restrictive pulmonary diseases, infectious and non-infectious pulmonary diseases, pulmonary vasculature disorders, and pleural cavity disorders, for example.

Embodiments of the invention are directed to methods and systems for assessing a presence of non-rhythm pulmonary diseases using a sensor system coupled to a respiratory therapy device. If the non-pulmonary disease is present based on the assessment, then a diagnosis of the non-pulmonary disease may be made. A non-rhythm pulmonary disease assessment system may be used to discriminate between types of non-rhythm pulmonary diseases, e.g., between obstructive pulmonary diseases and restrictive pulmonary diseases. The assessment system may additionally or alternatively be used to discriminate between non-rhythm pulmonary diseases of a particular type, e.g., between asthma and emphysema, both of which are pulmonary diseases of the obstructive type.

If the presence of a non-rhythm pulmonary disease is detected, then the progression of the disease may be monitored. Monitoring the progression of the non-rhythm pulmonary disease may involve, for example, evaluating one or more physiological changes or symptoms associated with the disease. Evaluating the physiological changes or symptoms may be accomplished by periodically sensing for conditions modulated by the symptoms or physiological changes and storing information about the sensed conditions. Monitoring disease progression may involve, for example, monitoring the severity of the disease, disease onset, changes during the course of the disease, regression, disease offset, and/or other aspects of the disease.

Embodiments of the invention utilize the sensor system of a patient-external respiratory therapy device to determine a presence of a non-rhythm pulmonary disease. The respiratory therapy device may comprise, for example, a gas therapy device, nebulizer, ventilator, positive airway pressure device, or other type of external respiration therapy device. In a preferred embodiment, the respiratory therapy device comprises a positive airway pressure device. Continuous positive airway pressure (CPAP) devices are frequently used to treat sleep apnea and/or other breathing rhythm disorders. A CPAP device may be used regularly during a patient's sleep time to prevent or treat sleep disordered breathing events. Use of a CPAP device for treatment of breathing rhythm disorders facilitates detection of non-rhythm pulmonary diseases. The CPAP device provides respiratory sensing functionality on a periodic basis that may be employed to sense conditions indicative of symptoms or physiological changes associated with non-rhythm pulmonary disease.

A typical CPAP device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example. The term xPAP will be used herein as a generic term for any device using forms of positive airway pressure (and negative pressure when necessary), whether continuous or otherwise.

Figure 3A:
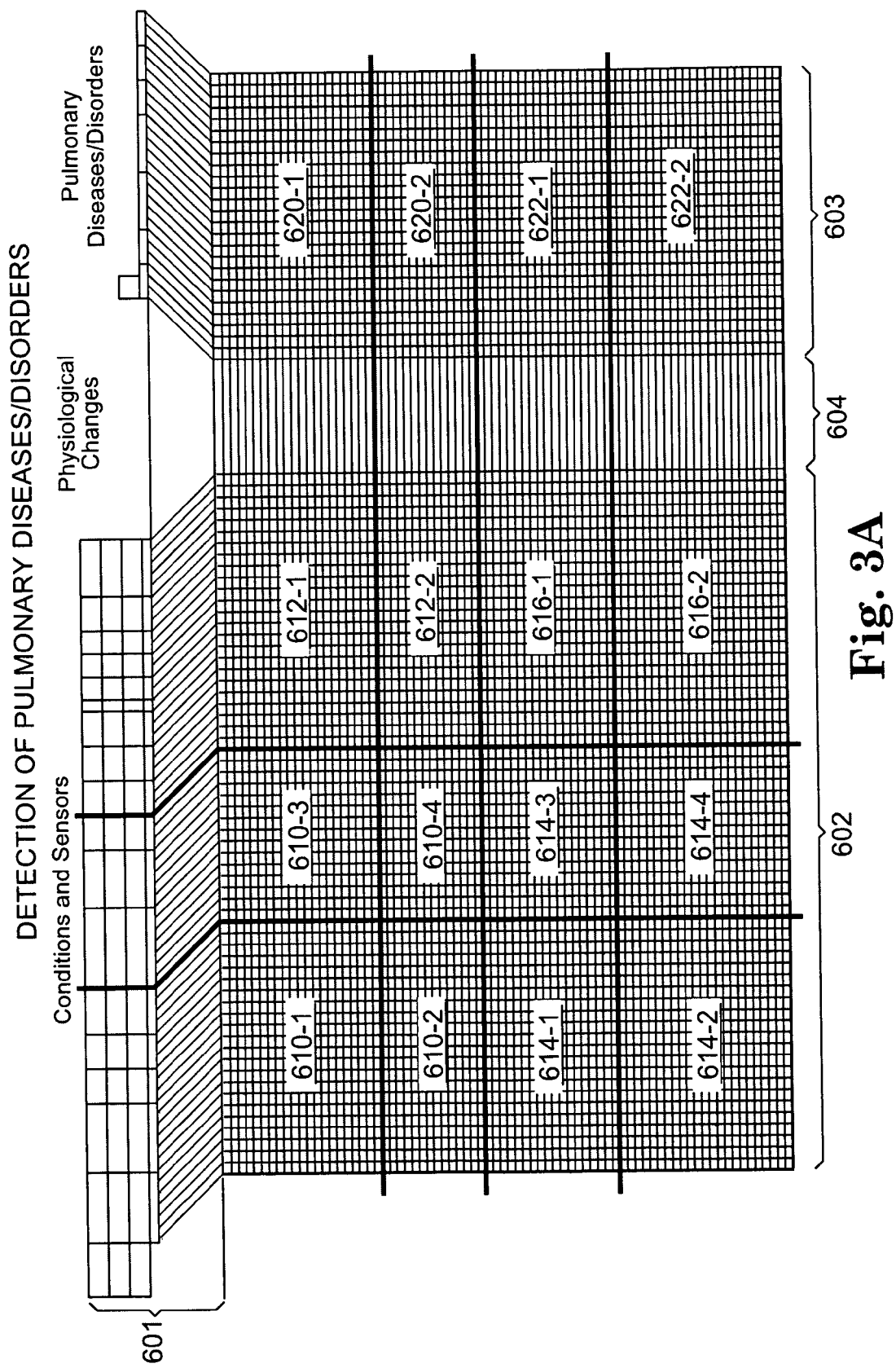
Figures 2, 3B:
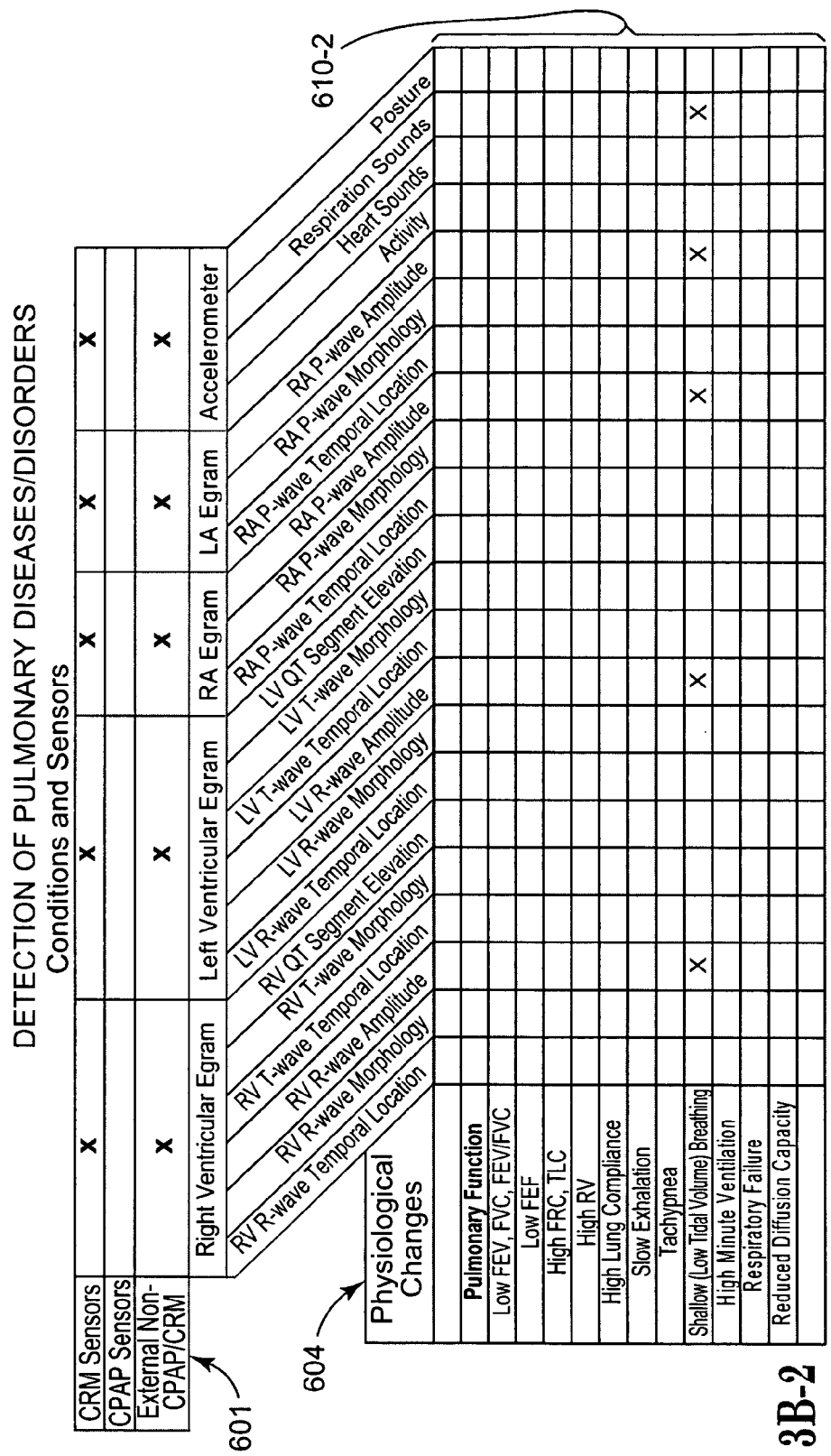
Figures 3, 3B:
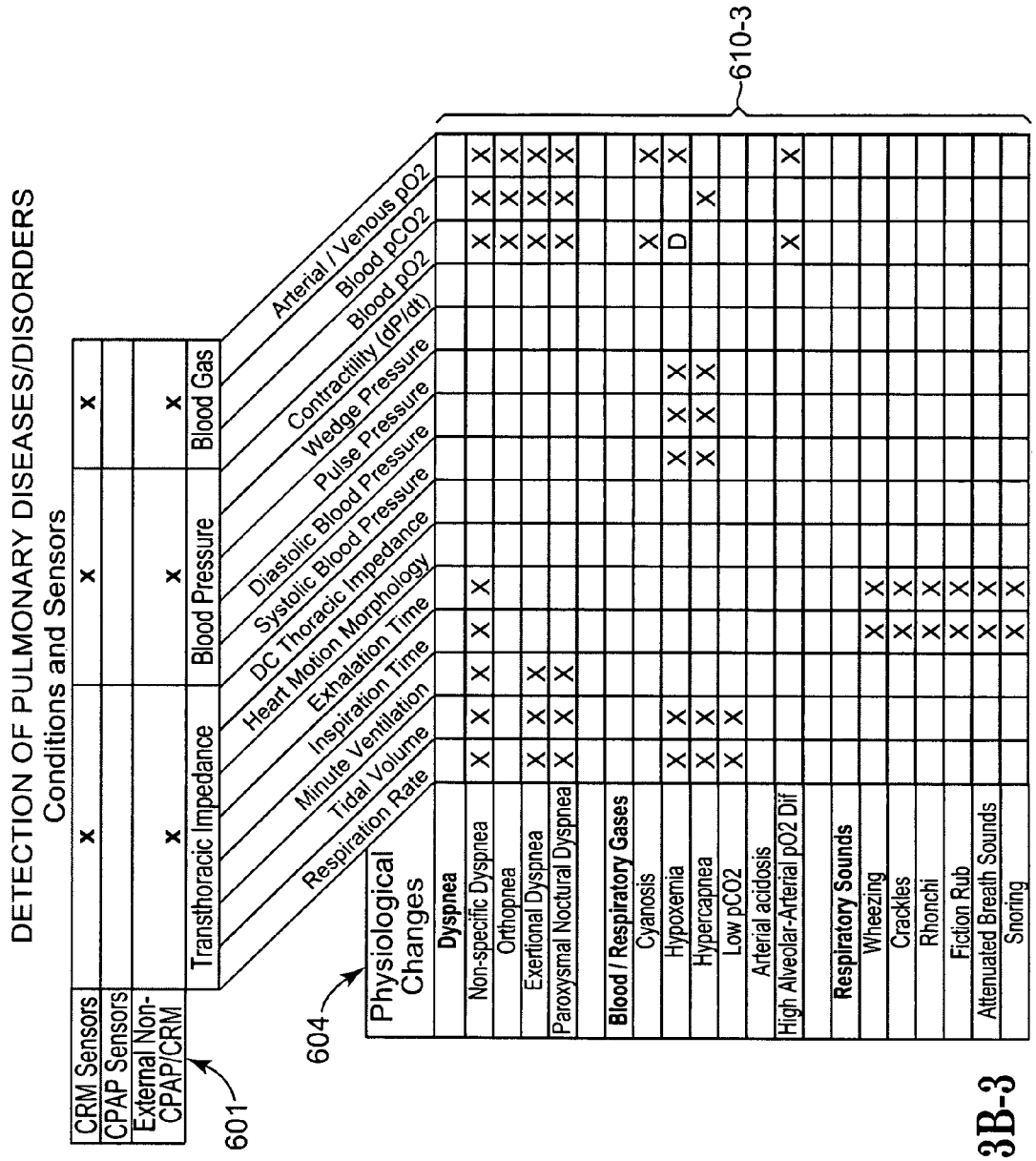
Figures 1, 3C:
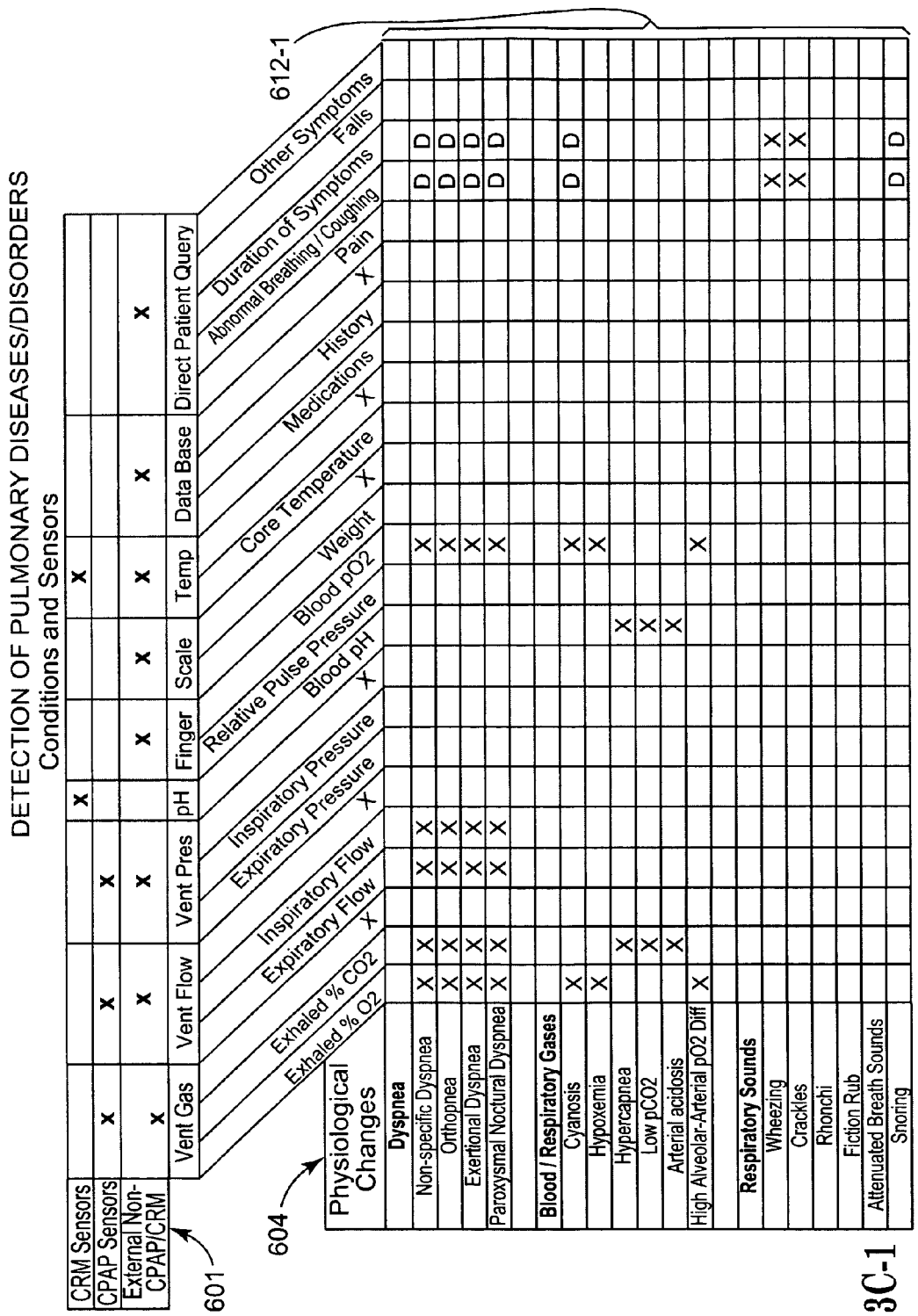
Figures 3, 3D, 4:
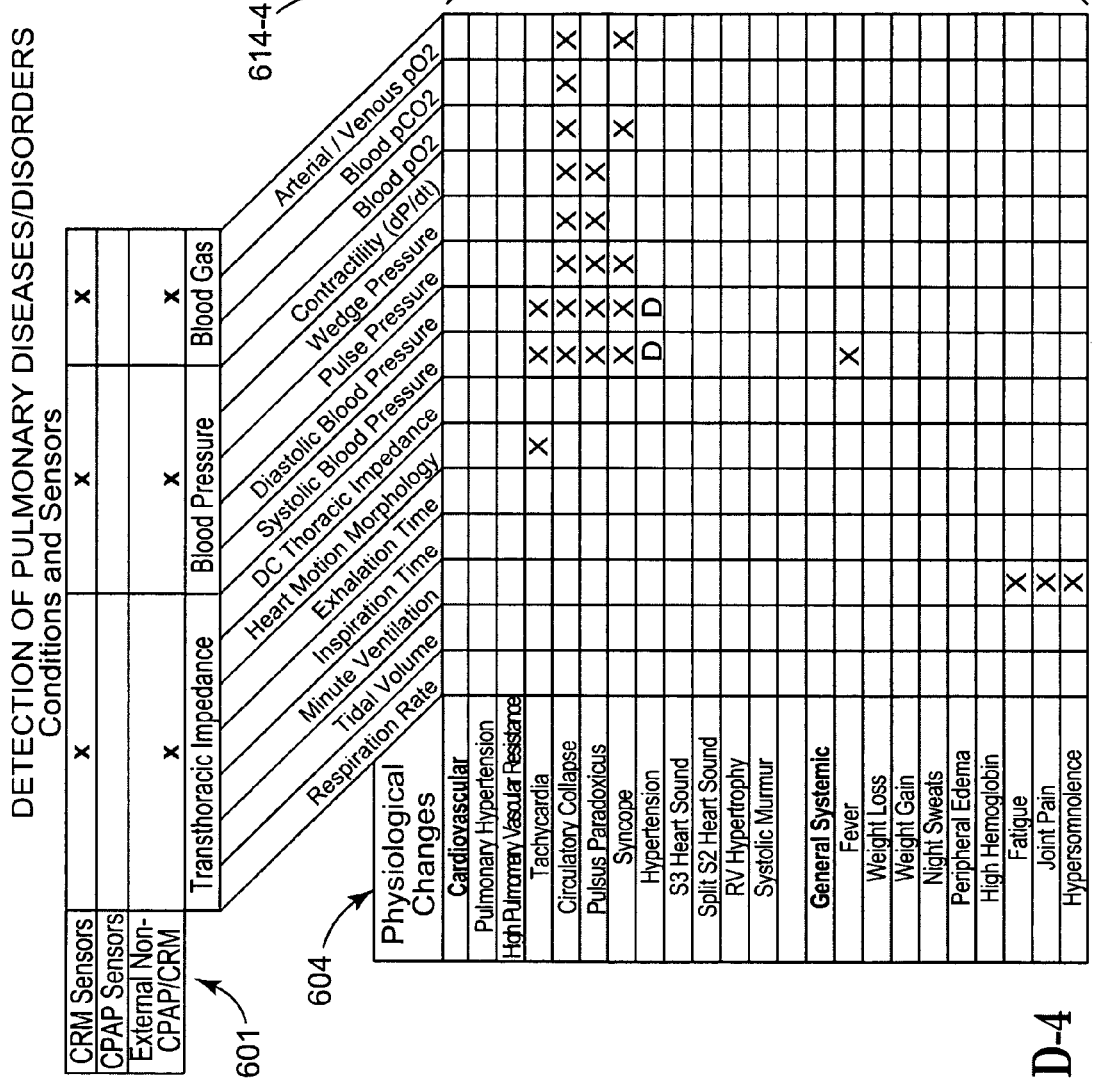

FIG. 1 is a flowchart illustrating a method of assessing a presence of a non-rhythm related pulmonary disease in accordance with embodiments of the invention. The method involves using 110 a respiratory therapy device to sense conditions associated with the non-rhythm related pulmonary disease and assessing 120 a presence of the non-rhythm pulmonary disease based on the sensed conditions.

The respiratory therapy device may include one or more sensors used to sense physiological conditions related to non-rhythm pulmonary disease. The respiratory therapy device sensors may include, for example, one or more ventilatory pressure sensors, capable of sensing inspiratory pressure and/or expiratory pressure, one or more ventilatory flow sensors, capable of sensing inspiratory flow and/or expiratory flow, one or more ventilatory gas sensors, capable of sensing exhaled $CO_2$ and/or exhaled $O_2$, among other sensors.

One or more of the physiological conditions sensed by the sensors of the respiratory therapy device may be measured and compared to criteria associated with presence of a non-rhythm pulmonary disorder. In some implementations, the one or more physiological conditions may be trended over time and the trended measurements compared to trend criteria. In some implementations, the criteria depend on relationships between the various measurements acquired using the sensors of the respiratory therapy device.

The measurements collected using the respiratory therapy device sensors may be stored in memory, along with sets of criteria used for assessing the presence of various non-rhythm pulmonary disorders. In one implementation, the memory storing the criteria sets and a diagnostic processor are disposed within the housing of the respiratory therapy device controller, for example. The diagnostic processor compares the measured conditions to the criteria sets in memory to assess the presence of various non-rhythm pulmonary disorders.

In one implementation, the measurements acquired by the respiratory therapy device may be transmitted to a remote device, such as an advanced patient management system. Diagnostic circuitry within the advanced patient management system may compare the conditions measured by the respiratory therapy device to the criteria sets stored in the APM system to assess the presence of non-rhythm pulmonary disorders.

According to one aspect of the invention, pulmonary function testing may be employed to detect physiological changes associated with the presence of pulmonary disease. Pulmonary function tests performed in a clinical setting may be used to evaluate lung mechanics, gas exchange, pulmonary blood flow, and blood gases and pH. They are used to evaluate patients in the diagnosis of pulmonary disease, assessment of disease development, or evaluation of the risk of pulmonary complications from surgery.

Pulmonary performance may be evaluated based on data acquired by the respiratory therapy device during normal and forced inspiration and expiration. From such data, pulmonary parameters including tidal volume, minute ventilation, forced expiratory volume, forced vital capacity, among other parameters may be determined.

Pulmonary function testing is conventionally performed in a clinical setting and measures values indicative of the ability of the lungs to exchange oxygen and carbon dioxide. The total lung capacity (TLC) is divided into four volumes. The tidal volume ($V_T$) is the volume inhaled or exhaled in normal quiet breathing. The inspiratory reserve volume (IRV) is the maximum volume that can be inhaled following a normal quiet inhalation. The expiratory reserve volume (ERV) is the maximum volume that can be exhaled following a normal quiet exhalation. The residual volume (RV) is the volume remaining in the lungs following a maximal exhalation. The vital capacity (VC) is the maximum volume that can be exhaled following a maximal inhalation; $VC=IRV+V_T+ERV$. The inspiratory capacity (IC) is the maximum volume that can be inhaled following a normal quiet exhalation; $IC=IRV+V_T$. The functional residual capacity (FRC) is the volume remaining in the lungs following a normal quiet exhalation; $FRC=ERV+RV$.

The vital capacity and its components ($V_T$, IRV, ERV, IC) are typically measured using a spirometer, which is a device that measures the volumes of air inhaled and exhaled. The FRC is usually measured by the helium dilution method using a closed spirometry system. A known amount of helium is introduced into the system at the end of a normal quiet exhalation. When the helium equilibrates throughout the volume of the system, which is equal to the FRC plus the volume of the spirometer and tubing, the FRC is determined from the helium concentration. This test may underestimate the FRC of patients with emphysema. The FRC can be determined quickly and more accurately by body plethysmography. The residual volume and total lung capacity are determined from the FRC.

In the forced vital capacity (FVC) maneuver, the patient exhales as forcefully and rapidly as possible, beginning at maximal exhalation. Several parameters are determined from the spirogram. The FVC is the total volume of air exhaled during the maneuver; it is normally equal to the vital capacity. The forced expiratory volume (FEV) is the volume expired during a specified time period from the beginning of the test. The times used are 0.5, 1, 2, and 3 seconds; corresponding parameters are $FEV_{0.5}$, $FEV_{1.0}$, $FEV_{2.0}$, and $FEV_{3.0}$. The maximal expiratory flow rate (MEFR) is the slope of the line connecting the points where 200 ml and 1200 ml have been exhaled; it is also called $FEF_{200-1200}$ (forced expiratory flow). The maximal midexpiratory flow rate (MMFR, MMF) is the slope of the line connecting the points where 25 percent and 75 percent of the FVC have been exhaled; it is also called $FEF_{25-75\%}$.

The Maximal Voluntary Ventilation (MVV) is the maximal volume of air that can be breathed by the patient, expressed in liters per minute; it was formerly called maximal breathing capacity (MBC). The patient breathes as rapidly and deeply as possible for 12 to 15 seconds and the volume exhaled is determined by spirometry.

Various parameters related to pulmonary performance, some of which may be measured using sensors of a respiratory therapy device include, for example, tidal volume, minute ventilation, inspiratory reserve volume, forced expiratory volume (FEV), residual volume, and forced vital capacity (FVC), among other parameters. According to one embodiment, testing of some pulmonary function parameters may be performed using the ventilation pressure and ventilation flow sensors of a CPAP device. The pulmonary function testing may be used, for example, to discriminate between restrictive and obstructive pulmonary disorders.

Because the results of pulmonary function tests vary with size and age, the normal values are calculated using prediction equations or nomograms, which give the normal value for a specific age, height, and sex. The prediction equations are derived using linear regression on the data from a population of normal subjects. The observed values are usually reported as a percentage of the predicted value. Abnormal test results may show either an obstructive or restrictive pattern. Sometimes, both patterns are present.

The results of pulmonary function testing, along with other measured physiological conditions, may be compared to initial or baseline results to detect changes in the patient's pulmonary status over time. The changes from baseline values may be used to discern a presence of disease processes. Further, over time, a database of information about relevant conditions and specific to the patient is established. The information may be used to develop sets of criteria specific to the patient and associated with the presence of a particular pulmonary disease processes. Thus, in some implementations, the system may learn to recognize the presence of disease based on the history of symptoms and/or physiological changes that occur in a particular patient.

FIG. 1B illustrates a normal respiratory pattern, having normal FEV and FVC. FIG. 1C illustrates an obstructive pattern. An obstructive pattern occurs when there is airway obstruction from any cause, as in asthma, bronchitis, emphysema, or advanced bronchiectasis; these conditions are grouped together in the nonspecific term chronic obstructive pulmonary disease (COPD). In this pattern, the residual volume is increased and the PV/TLC ratio is markedly increased. Owing to increased airway resistance, the flow rates are decreased. The FEV/FVC ratios, MMFR, and MEFR are all decreased; $FEV_{1.0}/FVC$ is less than 75 percent.

FIG. 1D illustrates a restrictive pattern. A restrictive pattern occurs when there is a loss of lung tissue or when lung expansion is limited as a result of decreased compliance of the lung or thorax or of muscular weakness. The conditions in which this pattern can occur include pectus excavatum, myasthenia gravis, diffuse idiopathic interstitial fibrosis, and space occupying lesions (tumors, effusions). In this pattern, the vital capacity and FVC are less than 80 percent of the predicted value, but the FEV/FVC ratios are normal. The TLC is decreased and the RV/TLC ratio is normal.

Embodiments of the invention utilize a patient-external respiratory therapy device to perform periodic pulmonary function testing. A CPAP or other external respiratory device may measure ventalitory pressure, ventilatory airflow, and/or ventilatory gas during periodic, e.g., nightly, therapy sessions. The ventalitory pressure and/or airflow measurements may be used to measure FVC and FEV during forced expiration. From these two parameters, FEV/FVC can be derived to differentiate obstructive versus restrictive respiratory patterns as shown in the FIGS. 1C and 1D. Other measurements that are possible using the respiratory device sensors include low forced expiratory flow (FEF), high functional residual capacity (FRC), total lung capacity (TLC), and high residual volume (RV).

In one embodiment, the patient may perform forced expirations while connected to the external respiratory device. During the forced expirations, circuitry in the external respiratory device may collect measurements, including FEV and FVC measurements.

In addition, the forced expiratory flow ($FEF_{25-75\%}$) may be measured. The middle half by volume of the total expiration is marked, and its duration is measured. The $FEF_{25-75\%}$ is the volume in liters divided by the time in seconds. In patients with obstructive diseases, the $FEF_{25-75\%}$ is generally greater than their expected values.

Circuitry incorporated in the CPAP device may be used to compare measured FVC, FEV and $FEF_{25-75\%}$ values derived from the pressure sensor and/or from the airflow sensor with predicted values from normal subjects in accordance with various embodiments. The comparison provides diagnostic information of lung mechanics. Data acquired by the CPAP device may be transmitted from the CPAP device to an advanced patient management (APM) system or other remote device.

Methods and systems for acquiring and using pulmonary function testing information, aspects of which may be utilized in connection with embodiments of the invention, are described in commonly owned U.S. Pat. No. 7,329,226, which is incorporated herein by reference.

Figure 2A:
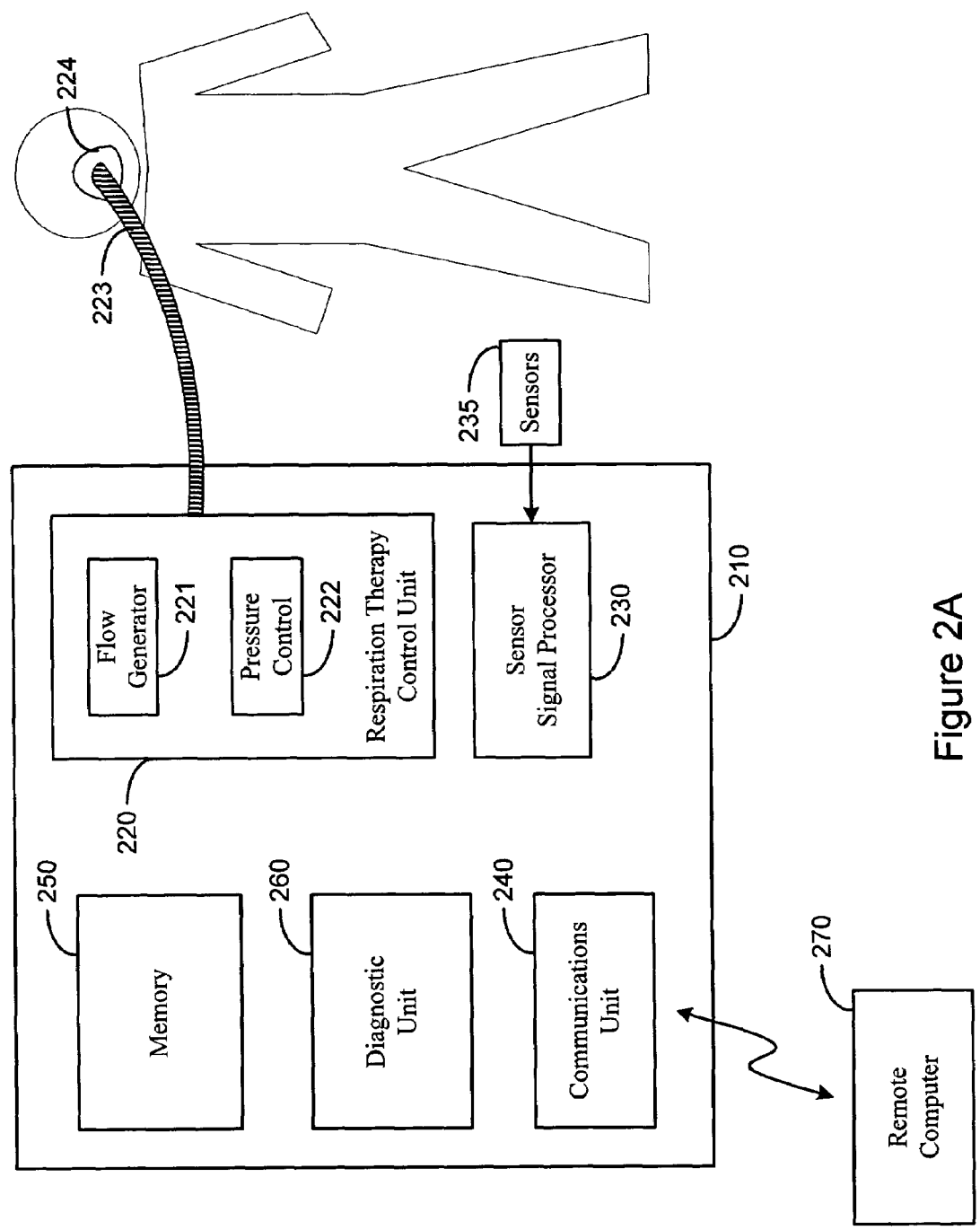
FIGS. 2A-2D are block diagrams of a pulmonary disease assessment system in accordance with embodiments of the invention.
Figure 2B:
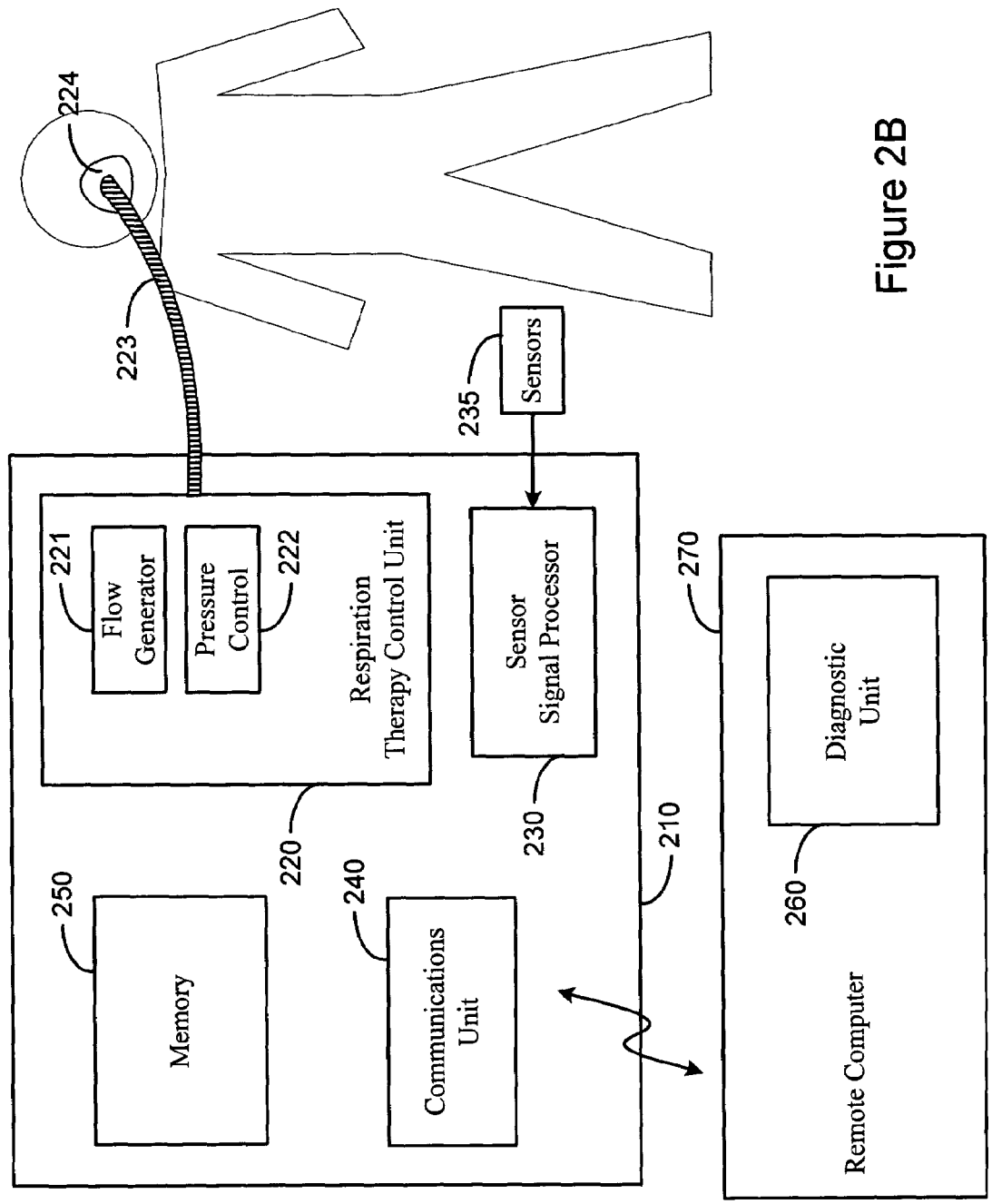

FIGS. 2A-2D are block diagrams of systems that may be used for non-rhythm pulmonary disease assessment in accordance with embodiments of the invention. FIG. 2A illustrates an external respiratory therapy device 210, e.g., a CPAP device, used to sense conditions associated with a non-rhythm pulmonary disease. The sensed conditions are evaluated by circuitry within the external respiratory therapy device 210 to assess a presence of the non-rhythm pulmonary disease.

The respiratory therapy device 210 is coupled to one or more sensors 235 configured to sense one or more conditions modulated by physiological changes and/or symptoms of the non-rhythm pulmonary disease. The sensors of the respiratory device used to sense the conditions may include, for example, ventalitory airflow, ventilatory pressure, ventilatory gas, and/or other conditions modulated by symptoms of the non-rhythm pulmonary disease.

A representative set of symptoms and/or physiological changes associated with non-rhythm pulmonary diseases may involve dyspnea (e.g., non-specific dyspnea, orthopnea, exertional dyspnea, paroxysmal nocturnal dyspnea), abnormal concentrations of blood or respiratory gases (e.g., cyanosis, hypoxemia, hypercapnea, low $pCO2$, arterial acidosis, high alveolar—arterial $pO2$ differential), pulmonary function dysfunction (e.g., low forced expiratory volume (FEV), forced vital capacity (FVC), FEV/FVC, low forced expiratory flow (FEF), high functional residual capacity (FRC), total lung capacity (TLC), high residual volume (RV), high lung compliance, slow exhalation, respiratory failure), other pulmonary conditions (e.g., ventilation-perfusion mismatch), and cardiovascular conditions (e.g., circulatory collapse).

Table 1 lists non-rhythm pulmonary disease symptoms or physiological changes, conditions indicative of the symptoms or physiological changes, and sensors of the respiratory therapy device that may be used to sense the conditions.

TABLE 1

| Symptom or Physiological Change | Condition | Sensor Used |
|---|---|---|
| Non-specific dyspnea | Exhaled % CO2 | CO2 sensor |
| Orthopnea | Exhaled % O2 | O2 sensor |
| Exertional dyspnea | Expiratory flow | Flowmeter |
| Paroxysmal nocturnal dyspnea | Inspiratory flow | Flowmeter |
| Cyanosis | Exhaled % O2 | O2 sensor |
| Hypoxemia | | |
| High alveolar-arterial pCO2 differential | | |
| Hypercapnea | Exhaled % CO2 | CO2 sensor |
| Low pCO2 | | |
| Arterial acidosis | | |
| Low FEV, FVC, FEV/FVC | Expiratory flow | Flowmeter |
| Low FEF | Inspiratory flow | Flowmeter |
| High FRC, TLC | Expiratory pressure | Pressure sensor |
| High RV | | |
| High lung compliance | Inspiratory pressure | Pressure sensor |
| Slow exhalation | | |
| Respiratory Failure | Exhaled % O2 | O2 sensor |
| Ventilation-perfusion mismatch | Exhaled % CO2 | CO2 sensor |
| Circulatory collapse | | |

The one or more sensors 235 are coupled to sensor signal processor circuitry 230 which may be configured to energize the sensors and to receive and condition signals generated by the sensors 235. The sensor signal processor circuitry 230 may comprise, for example, sensor driver circuitry, filters, sampling circuitry, and A/D converter circuitry. The sensor signals may be averaged, filtered, or otherwise processed by the signal processor circuitry 230 prior to use by other components of the respiratory therapy device 210.

The respiratory therapy device 210, illustrated in FIG. 2A as a positive airway pressure (xPAP) device includes a respiration therapy control unit 220. The respiration therapy control unit 220 comprises a flow generator 221 that pulls in air through a filter. The flow generator 221 is controlled by the pressure control circuitry 222 to deliver an appropriate air pressure to the patient. Air flows through tubing 223 coupled to the xPAP device 210 and is delivered to the patient's airway through a mask 224. In one example, the mask 224 may be a nasal mask covering only the patient's nose. In another example, the mask 224 covers the patient's nose and mouth. Other air delivery systems are also possible.

Continuous positive airway pressure (CPAP) devices deliver a set air pressure to the patient. The pressure level for the individual patient may be determined during a titration study, for example. Such a study may take place in a sleep lab, and involves determination by a sleep physician or other professional of the optimum airway pressure for the patient. The CPAP device pressure control is set to the determined level. When the patient uses the CPAP device, a substantially constant airway pressure level is maintained by the device. The constant air pressure acts a pneumatic splint to keep soft tissue in the patient's throat from collapsing and obstructing the airway.

Autotitration PAP devices are similar to CPAP devices, however, the pressure controller for autotitration devices automatically determines the air pressure delivered to the patient. Instead of maintaining a constant pressure, the autotitration PAP device evaluates sensor signals and the changing needs of the patient to deliver a variable positive airway pressure. Autotitration PAP and CPAP are often used to treat sleep disordered breathing, for example.

Bi-level positive airway pressure (bi-PAP) devices provide two levels of positive airway pressure. A higher pressure is maintained while the patient inhales. The device switches to a lower pressure during expiration. Bi-PAP devices are used to treat a variety of respiratory dysfunctions, including chronic obstructive pulmonary disease (COPD), respiratory insufficiency, and ALS or Lou Gehrig's disease, among others.

The xPAP device may include a memory 250 that stores criteria used in the assessment of pulmonary disease. The memory may additionally or alternatively store information related to measurements of the conditions sensed by the xPAP device.

In accordance with various embodiments of the invention, the xPAP device 210 may include a diagnostic unit 260 that evaluates patient conditions sensed by the sensors 235 and assesses a presence of a non-rhythm pulmonary disease. For example, the diagnostic unit 260 may compare the measured conditions to sets of criteria indicative of non-rhythm pulmonary diseases. If the measured conditions are consistent with a particular set of criteria, the diagnostic unit may indicate that the non-rhythm pulmonary disease associated with the particular criteria set is present.

The xPAP device 210 may include a communications unit 240 for communicating with one or more separate devices 270, such as a device programmer or a cooperating patient-external or patient-internal monitoring, diagnostic and/or therapeutic device. Communication between cooperating devices allows the xPAP device 210 to provide information to the cooperating device or devices or to control therapy delivered by the cooperating devices, for example. In one scenario, the xPAP device 210 may transmit to a cooperating therapy device information about the presence of a non-rhythm pulmonary disease/disorder. The therapy device may adjust therapy delivered by the device based on the presence of the non-rhythm pulmonary disease/disorder. Additionally, or alternatively, the xPAP device 210 may adjust the respiration therapy delivered to the patient based on the non-rhythm pulmonary disease assessment.

In one implementation, a system for assessment of non-rhythm pulmonary disorders may be used within the structure of an advanced patient management system. In this implementation, an advanced patient management system includes a remote computer system that allows a physician to remotely monitor cardiac, respiratory, and other patient functions. The advanced patient management system may have the capability of assessing the presence of various non-rhythm pulmonary diseases based on respiration measurements acquired by the xPAP device 210 and transmitted to the APM system. Systems and methods involving advanced patient management techniques are described in U.S. Pat. Nos. 6,336,903, 6,312,378, 6,270,457, and 6,398,728 which are incorporated herein by reference in their respective entireties.

As previously discussed, the xPAP device 210 may include a memory 250 for storing data related to the non-rhythm pulmonary disease. For example, the xPAP device 210 may initiate collection and storage of data hourly, nightly, weekly, or according to some other time schedule that corresponds to the patient's usage times of the respiratory therapy device. Typically an xPAP device is used nightly for treatment of sleep apnea and/or other breathing rhythm disorders. The xPAP device 210 may collect data from the sensors 235 during one or more periods of time that the device is used. The presence of the non-rhythm pulmonary disease may be assessed based on the collected data. Assessment of the presence of the non-rhythm pulmonary disease may involve assessment of the severity of the disease, disease onset, changes during the course of the disease, regression, disease offset, and/or other aspects of the disease.

In one implementation, the diagnosis unit 260 is a component of the respiratory therapy device 210, as illustrated in FIG. 2A. In another implementation, the diagnosis unit 260 may be configured as a component of a device 270 separate from the respiratory therapy device 210. The latter implementation is illustrated in the block diagram of FIG. 2B. In this implementation, the respiratory therapy device 210 may transmit information about conditions sensed by the respiratory therapy device 210 to the diagnosis unit 260 of a remotely located device 270. The diagnosis unit 260 assesses the non-rhythm pulmonary disease presence based on the transmitted information.

The remote device 270 may comprise a patient-external or patient-internal medical device. The remote device 270 may be configured, for example, as a cardiac diagnostic and/or therapeutic device. In one configuration, for example, the remote device may comprise a cardiac rhythm management system, such as a pacemaker, defibrillator, and/or cardiac resynchronizer.

Figure 2C:
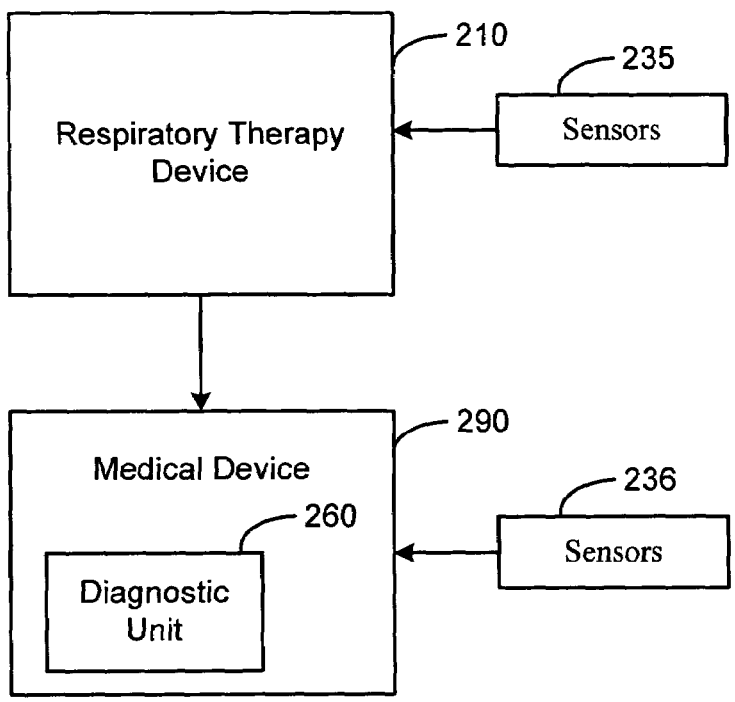
Figure 2D:
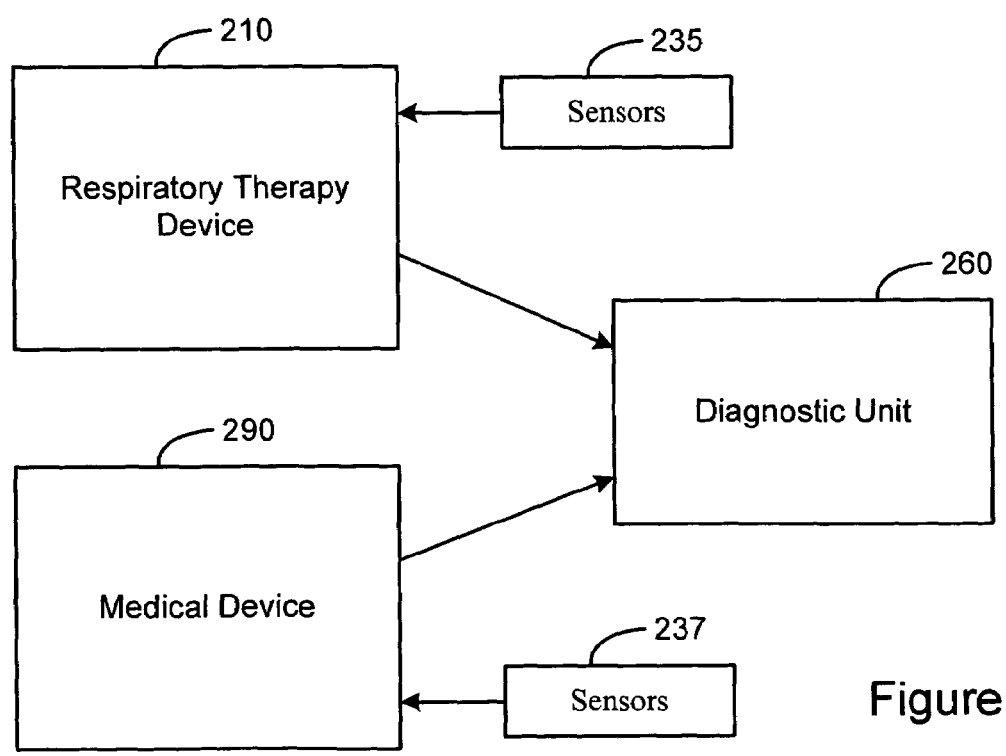

The block diagrams of FIGS. 2C and 2D illustrate other exemplary arrangements that may be used for pulmonary disease assessment in accordance with embodiments of the invention. The system illustrated in FIG. 2C includes a respiratory therapy device 210 and a medical device 290 remote from the respiratory therapy device 210. In this example, both the respiratory therapy device 210 and the medical device 290 are equipped with sensors 235, 236 for sensing conditions associated with symptoms of one or more non-rhythm pulmonary diseases. For example, the respiratory therapy device 210 and the additional medical device 290 may each sense a subset of the conditions listed in Table 1. The respiratory therapy device 210 may transmit its sensed condition information to the medical device 290 over a wired or wireless communications link. The medical device 290 includes a diagnostic unit 260 configured to assess a presence of one or more non-rhythm pulmonary diseases. The diagnostic unit 260 may assess the non-rhythm pulmonary diseases, for example, by comparing sensed conditions to one or more sets of criteria indicative of the non-rhythm pulmonary diseases as previously described.

The block diagram of FIG. 2D illustrates a further exemplary arrangement of a pulmonary disease assessment system. In this example, the system includes a respiratory therapy device 210 and an additional medical device 290, e.g., a therapeutic or monitoring device. The respiratory therapy device 210 and the additional medical device 290 communicate with a diagnostic unit 260, such as a diagnostic unit of an APM system. The respiratory therapy device 210 and the additional medical device 290 are each equipped with sensors 235, 236 for sensing conditions associated with one or more non-rhythm pulmonary diseases. The respiratory therapy device 210 and the medical device 290 may transmit sensed condition information to the diagnostic unit 260 through wireless or wired communication links. The pulmonary disease diagnostic unit 260 is configured to use the information transmitted by the respiration therapy device 210 and the medical device 290 to assess the presence of one or more non-rhythm pulmonary diseases.

Assessment of conditions indicative of non-rhythm pulmonary diseases/disorders may include assessing the patient's pulmonary function as previously described. The charts provided in FIGS. 3A-3G-2 illustrate conditions and sensors that may be used to determine physiological changes associated with various non-rhythm pulmonary diseases and disorders. The charts depicted in FIGS. 3A-3G-2 illustrate relationships between various physiological changes and/or disease symptoms associated with non-rhythm pulmonary diseases. FIG. 3A lists representative sets of non-rhythm pulmonary diseases that may be assessed in accordance with embodiments of the invention. The representative set of non-rhythm pulmonary diseases that may be assessed includes, for example, obstructive pulmonary diseases (e.g., chronic bronchitis, emphysema, asthma), restrictive pulmonary diseases (e.g., sarcoidosis, pulmonary fibrosis, pneumoconiosis), infections pulmonary diseases (e.g., bronchitis, pneumonia, bronchiolitis, tuberculosis, and bronchiectasis), pulmonary vasculature diseases (e.g., pulmonary hypertension, pulmonary edema, pulmonary embolism, atalectasis), and diseases of the pleural cavity (e.g., pleural effusion, pneumothorax, and hemothorax).

The non-rhythm pulmonary diseases listed in FIG. 3A are cross-referenced with the physiological changes and/or symptoms associated with the non-rhythm pulmonary disease. The physiological changes and/or symptoms are cross referenced with conditions indicative of the physiological changes and/or symptoms. Sensors used to sense the conditions indicative of the physiological changes or symptoms are provided in FIG. 3A. Sensors of the respiratory therapy device may include, for example, ventilation gas, ventilation flow and/or ventilation pressure sensors, or other sensors for example.

The left section 602 of FIG. 3A illustrates various conditions that may be sensed using sensors of a respiratory therapy device (CPAP), a cardiac device (CRM), or an external non-CPAP, non-CRM device. The top section 601 lists various conditions that may be sensed and information about sensors used to sense the conditions. The center section 604 of FIG. 3A provides physiological changes and/or symptoms that may be evaluated using the conditions listed in the left section 602. The right section 603 of FIG. 3A provides pulmonary diseases/disorders. The presence of the pulmonary diseases/disorders of the right section 603 may be assessed based on the physiological changes and/or symptoms of the center section 604.

Figures 1, 3E:
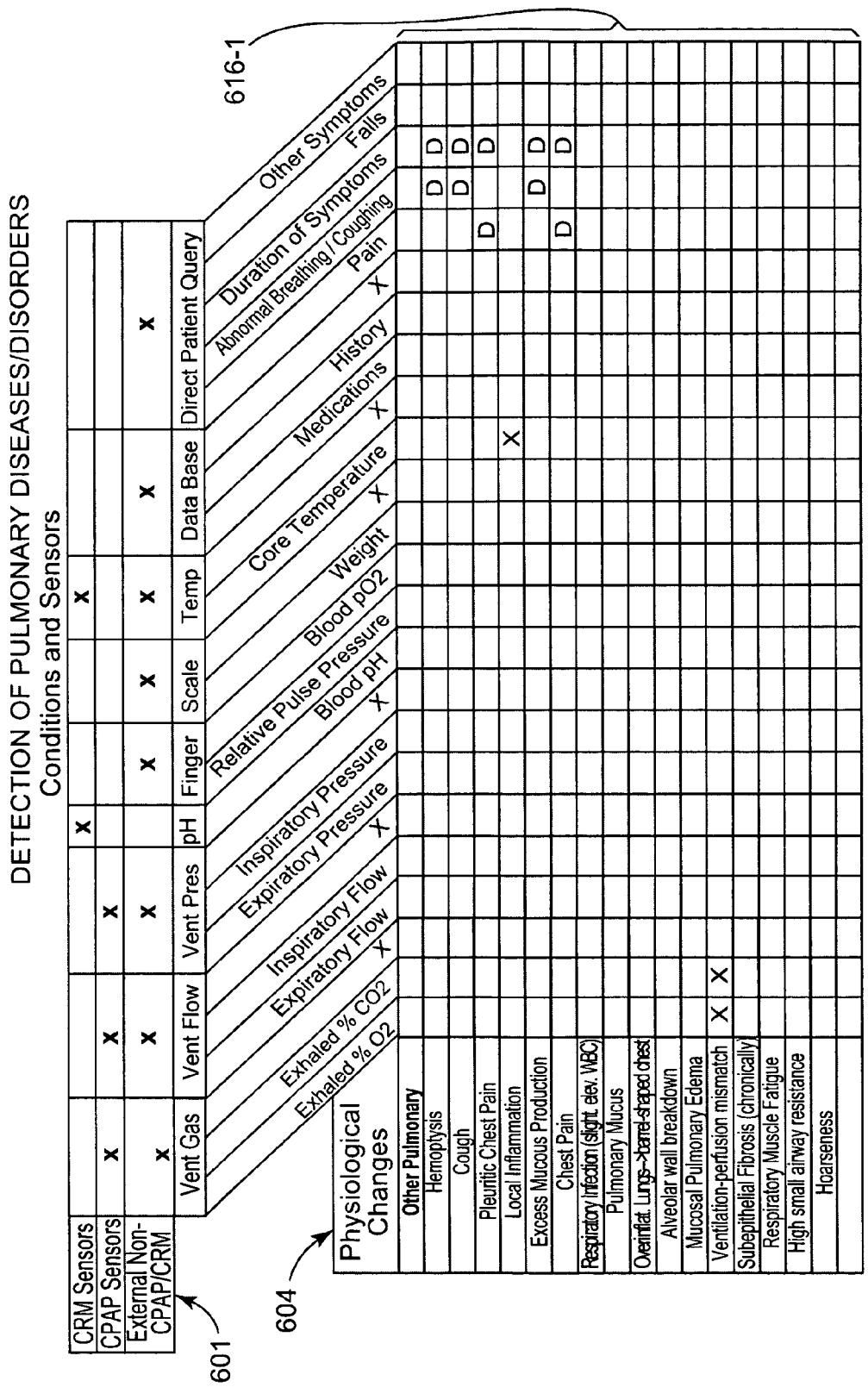
Figures 2, 3E:
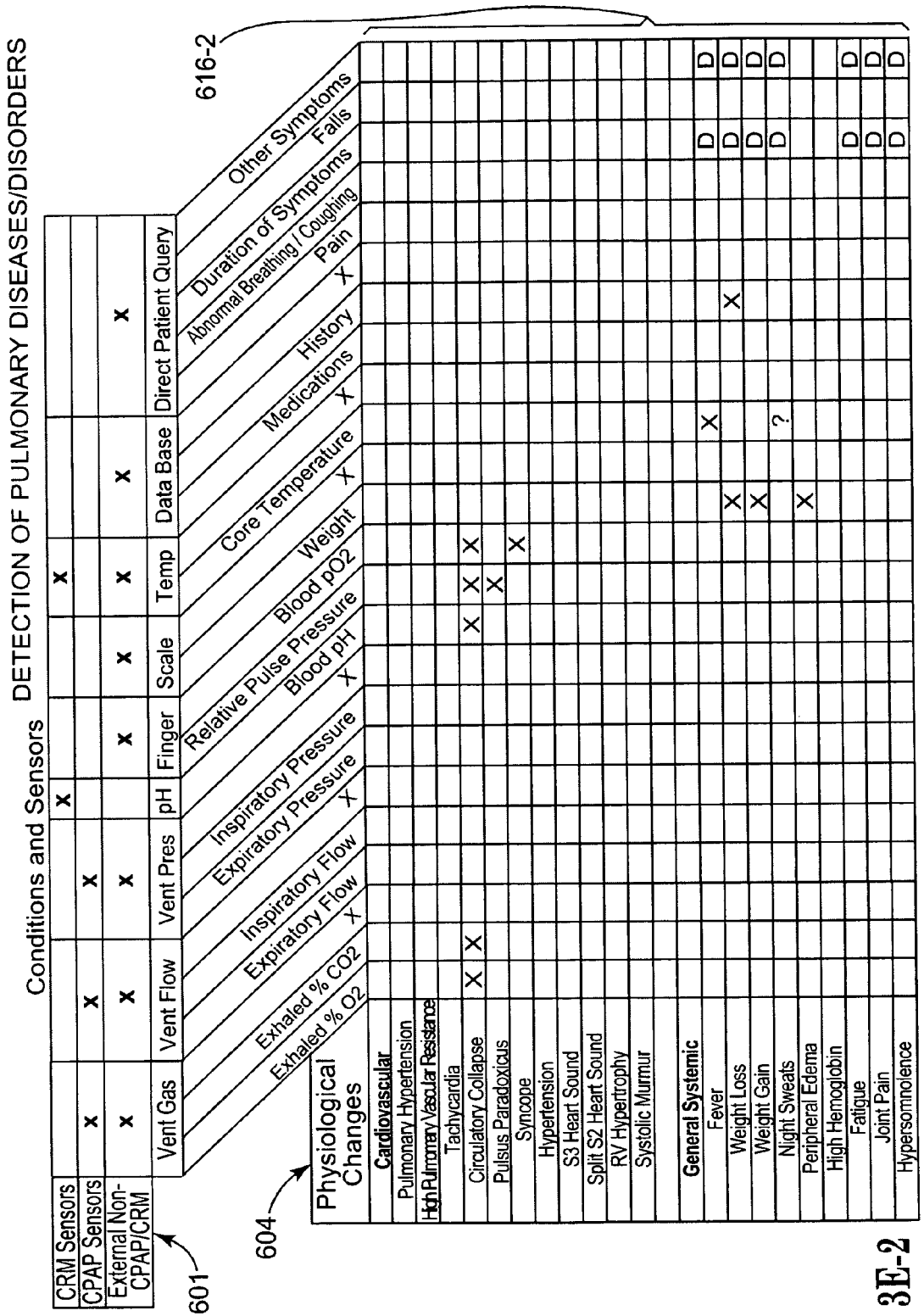
Figure 3F-1:
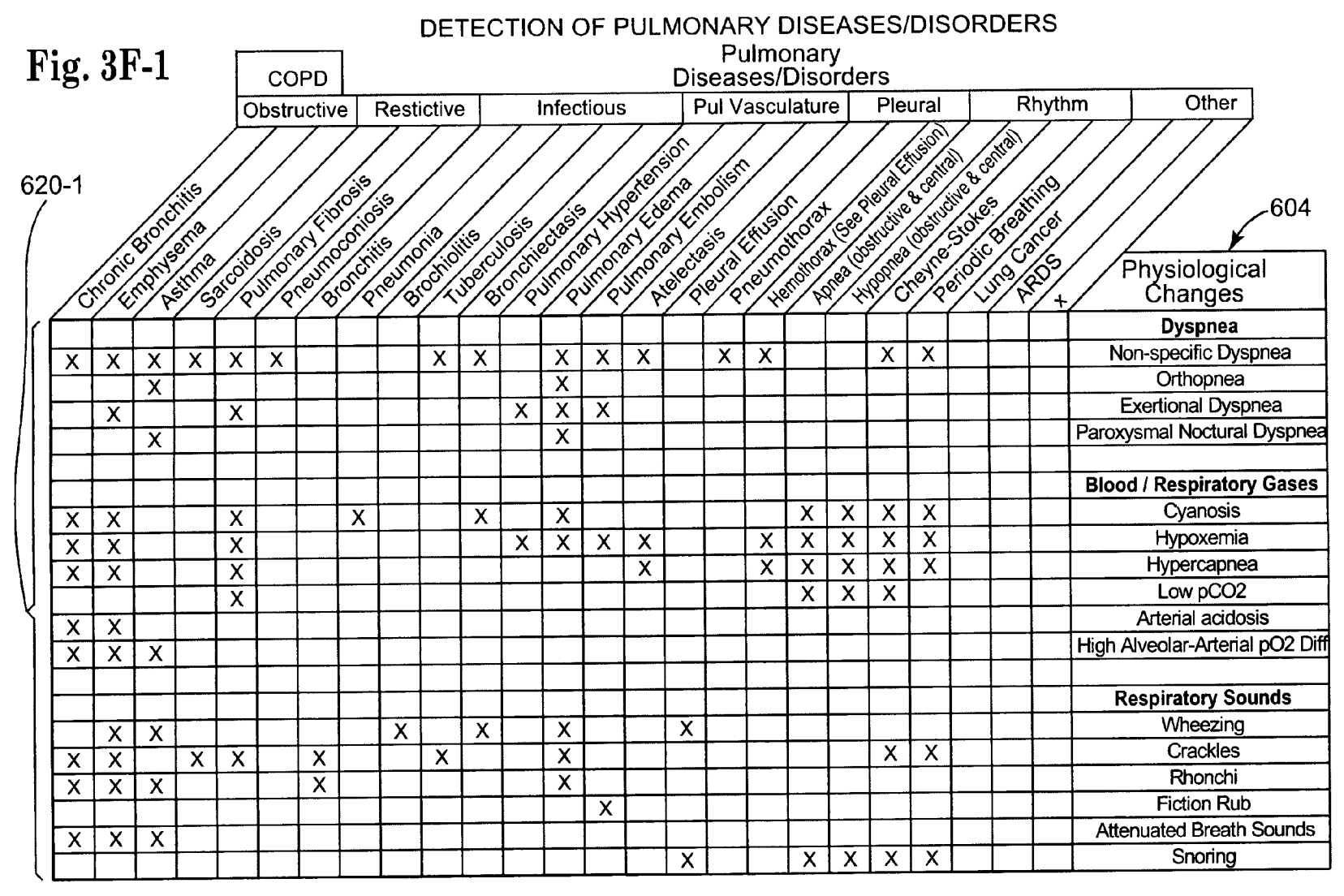
Figures 2, 3G:
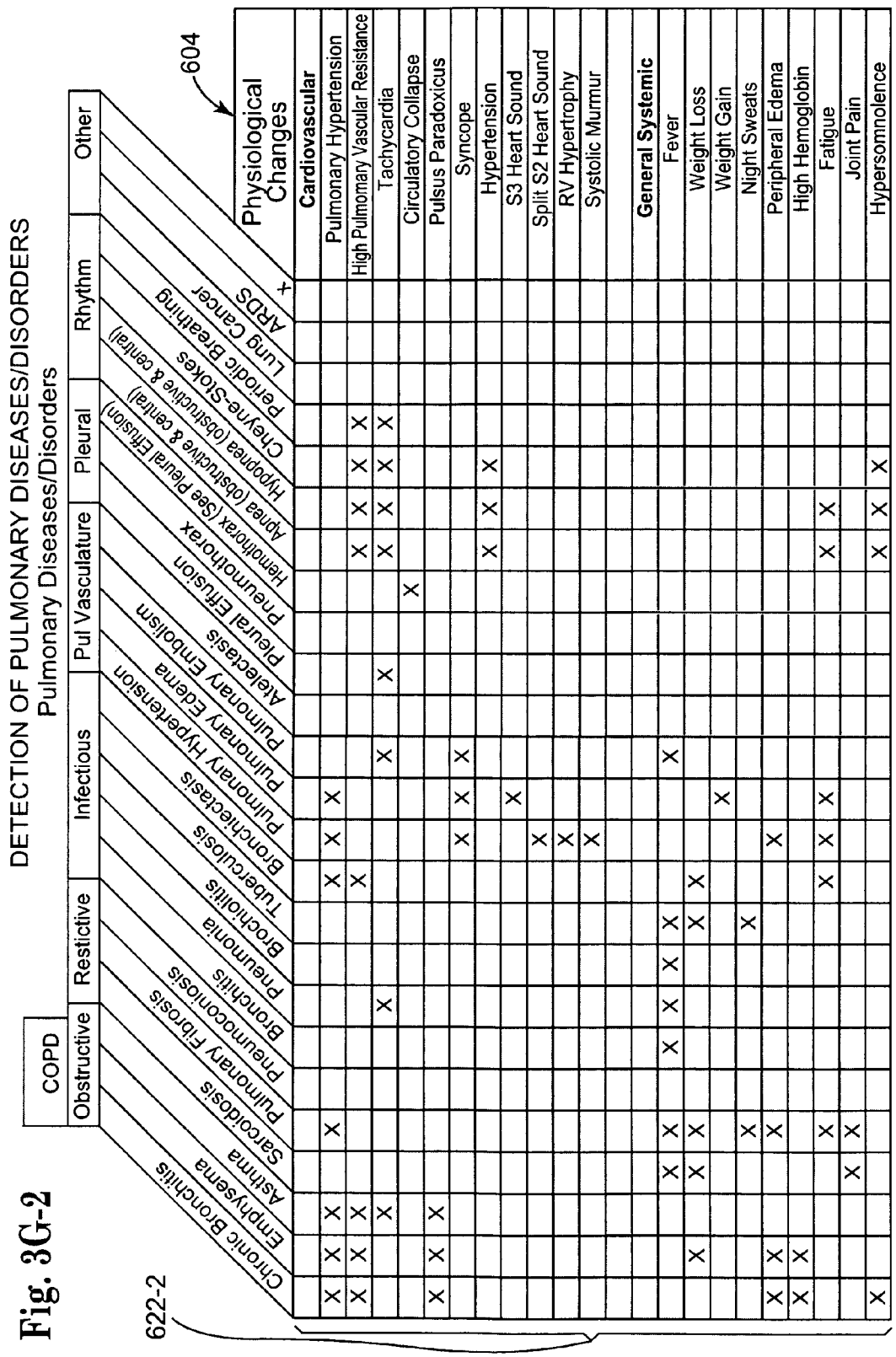

For legibility, the left and right sections 602, 603 of FIG. 3A are divided into sixteen portions, FIGS. 3B-1-3G-2. FIGS. 3B-1 to 3B-4 represent the upper left portions 610-1 to 610-4 of the left section 602 of FIG. 3A. FIGS. 3C-1 to 3C-2 represent the upper right portions 612-1 to 612-2 of the left section 602 of FIG. 3A. FIGS. 3D-1 to 3D-4 represent the lower left portions 614-1 to 614-4 of the left section 602 of FIG. 3A. FIGS. 3E-1 to 3E-2 represent the lower right portions 616-1 to 616-2 of the left section 602 of FIG. 3A. FIGS. 3F-1 to 3F-2 represent the upper portions 620-1 to 620-2 of the right section 603 of FIG. 3A. FIGS. 3G-1 to 3G-2 represent the lower portions 622-1 to 622-2 of the right section 603 of FIG. 3A. Relevant portions of the center section 604 and the top section 601 of FIG. 3A appear in each of the FIGS. 3B-1-3G-2 for convenience.

An example of how FIGS. 3A-3G-2 may be used follows. Referring to FIGS. 3F-1 to 3G-2, the restrictive pulmonary disorder pneumoconiosis produces the physiological changes non-specific dyspnea (FIG. 3F-1) and cough (FIG. 3G-1). Non-specific dyspnea (FIG. 3F-1) and cough (FIG. 3G-1) are indicated by marks in the column denoted pneumoconiosis in FIGS. 3F-1 and 3G-2, respectively. Non-specific dyspnea may be detected based on one or more of the conditions listed in the row for non-specific dyspnea illustrated in FIGS. 3B-1, 3B-3 and 3C-1. The conditions include duration of symptoms, abnormal breathing/coughing, blood pO2, inspiratory flow, expiratory flow, exhaled % CO2 and exhaled % O2, illustrated in FIG. 3C-*l*. The conditions also include arterial/venous pO2, blood pCO2, blood pO2, exhalation time, inspiration time, minute ventilation, tidal volume, respiration rate, FIG. 3B-3, and/or respiration sounds illustrated in FIG. 3B-1.

The presence of a disorder/disease, such as those listed in FIGS. 3A-3G-2, may be assessed by based on physiological changes and/or symptoms associated with the disorder/disease. The physiological changes and/or symptoms may be detected using conditions sensed by a sensor system of a respiratory therapy alone or in combination with the sensor systems of other therapeutic or diagnostic medical devices. If the sensed conditions indicate that the physiological changes or symptoms of a disease or disorder are consistent with a threshold level, the presence of the disease or disorder may be determined.

In another example, assessment of disease presence may be based on relative changes in one or more conditions indicative of physiological changes or symptoms caused by the disease. For example, assessment of a presence of a disease or disorder may be accomplished by evaluating the changes in conditions indicative of physiological changes or symptoms caused by the disease. The changes in the one or more conditions may be compared to threshold criteria. If changes in the conditions indicative of physiological changes or symptoms caused by the disease are consistent with threshold levels, a presence of the disease or disorder may be determined.

In a further example, the threshold criteria may involve relationships between the conditions indicative of physiological changes or symptoms caused by the disease. The presence of a disease may be assessed by evaluating relationships between conditions indicative of physiological changes or symptoms caused by the disease. For example, assessment of a disease may involve the determination that levels or amounts of two or more conditions have a certain relationship with one another. If relationships between the conditions indicative of physiological changes or symptoms caused by the disease are consistent with threshold relationship criteria, the disease or disorder may be present.

In accordance with various embodiments of the invention, the presence of a non-rhythm pulmonary disease, such as those listed in FIGS. 3A-3G-2, may be assessed by evaluating conditions indicative of the non-rhythm pulmonary disease sensed using a respiration therapy device. In one example, the presence of a non-rhythm pulmonary disease may be assessed by comparing conditions indicative of physiological changes or symptoms caused by the disease to threshold criteria. If the conditions indicative of physiological changes or symptoms caused by the disease are consistent with threshold levels, the system may determine that the non-rhythm pulmonary disease or disorder is present.

In another example, assessment of disease presence may be based on relative changes in one or more conditions indicative of physiological changes or symptoms caused by the disease. For example, diagnosis of a non-rhythm pulmonary disease may be effected by evaluating the changes in conditions indicative of physiological changes or symptoms caused by the disease. The changes in the one or more conditions may be compared to threshold criteria. If changes in the conditions indicative of physiological changes or symptoms caused by the disease are consistent with threshold levels, the non-rhythm pulmonary disease or disorder may be present.

In a further example, the threshold criteria may involve relationships between the conditions indicative of physiological changes or symptoms caused by the disease. The presence of a non-rhythm pulmonary disease may be assessed by evaluating relationships between conditions indicative of physiological changes or symptoms caused by the disease. For example, assessment of a disease may involve the determination that levels or amounts of two or more conditions have a certain relationship with one another. If relationships between the conditions indicative of physiological changes or symptoms caused by the disease are consistent with threshold relationship criteria, the non-rhythm pulmonary disease or disorder may be present.

Figure 4A:
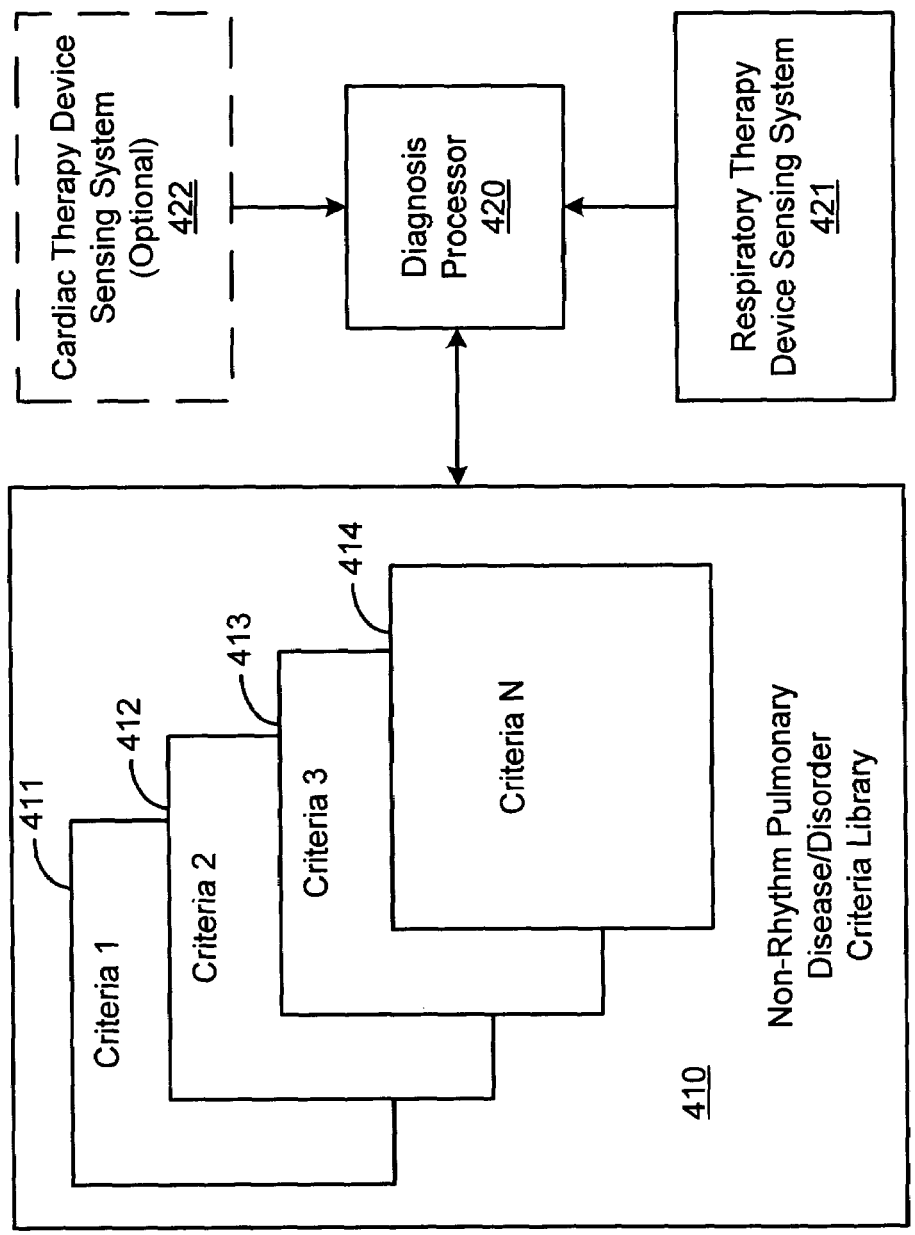
FIG. 4A is a block diagram of a system that may be used to assess a pulmonary disease in accordance with embodiments of the invention.

FIG. 4A illustrates a system for assessing a presence of a non-rhythm pulmonary disease/disorder in accordance with embodiments of the invention. The system includes a diagnosis processor 420 that receives information from a sensing system of a respiratory device 421. The sensing system 421 measures one or more conditions associated with a non-rhythm pulmonary disease or disorder. In some embodiments, the diagnosis processor may also receive sensory information from another device 422, such as a cardiac therapy device.

The diagnosis processor 420 accesses a criteria library 410. The criteria library 410 stores sets of criteria 411-414 respectively associated with various non-pulmonary diseases/disorders. FIGS. 4B-4K illustrate criteria sets that may be used to assess a presence of non-rhythm pulmonary disease in accordance with embodiments of the invention. The exemplary criteria sets may be used to assess the presence of chronic bronchitis (FIG. 4B), emphysema (FIG. 4C), asthma (FIG. 4D), pulmonary fibrosis (FIG. 4E), pulmonary hypertension (FIG. 4F), pulmonary edema (FIG. 4G), pulmonary embolism (FIG. 4H), atelectasis (FIG. 4I), and hemothorax (FIG. 4J). The charts of FIGS. 4A-4J list physiological changes or symptoms associated with the non-rhythm pulmonary disease in the left hand column, conditions used to detect the particular physiological change or symptom in the middle column, and the respiration therapy device sensor used to sense the condition in the right hand column.

Using FIG. 4J as a representative example, the presence of atelectasis may be assessed based on the symptoms non-specific dyspnea, hypoxemia, and/or hypercapnia. Non-specific dyspnea may be detected based on one or more of the following criteria: exhaled % CO2, exhaled % O2, expiratory flow, and/or inspiratory flow. The levels of one or more of these conditions may be compared to threshold levels for assessment of atelectasis. Other symptoms associated with atelectasis include hypoxemia, which may be determined based on comparison of the patient's exhaled % O2 to a threshold criterion, and hypercapnia, which may be determined based on comparison of the patient's exhaled % CO2 to a threshold criterion.

The criteria listed in FIGS. 4B-4J involve conditions that may be detected using sensors of a respiratory therapy device, such as a CPAP device. The non-rhythm pulmonary disease assessment system described herein may use one or more additional sensors and/or devices other than the respiratory therapy device to enhance disease assessment, such as those indicated in FIGS. 3A-3G-2. In one example, conditions detected using an external respiratory therapy device, e.g., CPAP device, may be used along with conditions detected using an implantable cardiac device, e.g., pacemaker or defibrillator to assess the presence of a non-rhythm pulmonary disease. In another example, conditions detected using an external respiratory therapy device, e.g., CPAP device, may be used along with conditions detected using an additional external device.

FIG. 4K illustrates an exemplary criteria set for assessing a presence of tuberculosis. Tuberculosis may be assessed based on conditions sensed using a respiratory therapy device in addition to conditions sensed using other devices. FIG. 4K lists physiological changes or symptoms associated with tuberculosis in the left hand column, conditions used to assess a presence of tuberculosis in the middle column, and the respiration therapy device sensor or other device sensor used to sense the condition in the right hand column.

Figure 5A:
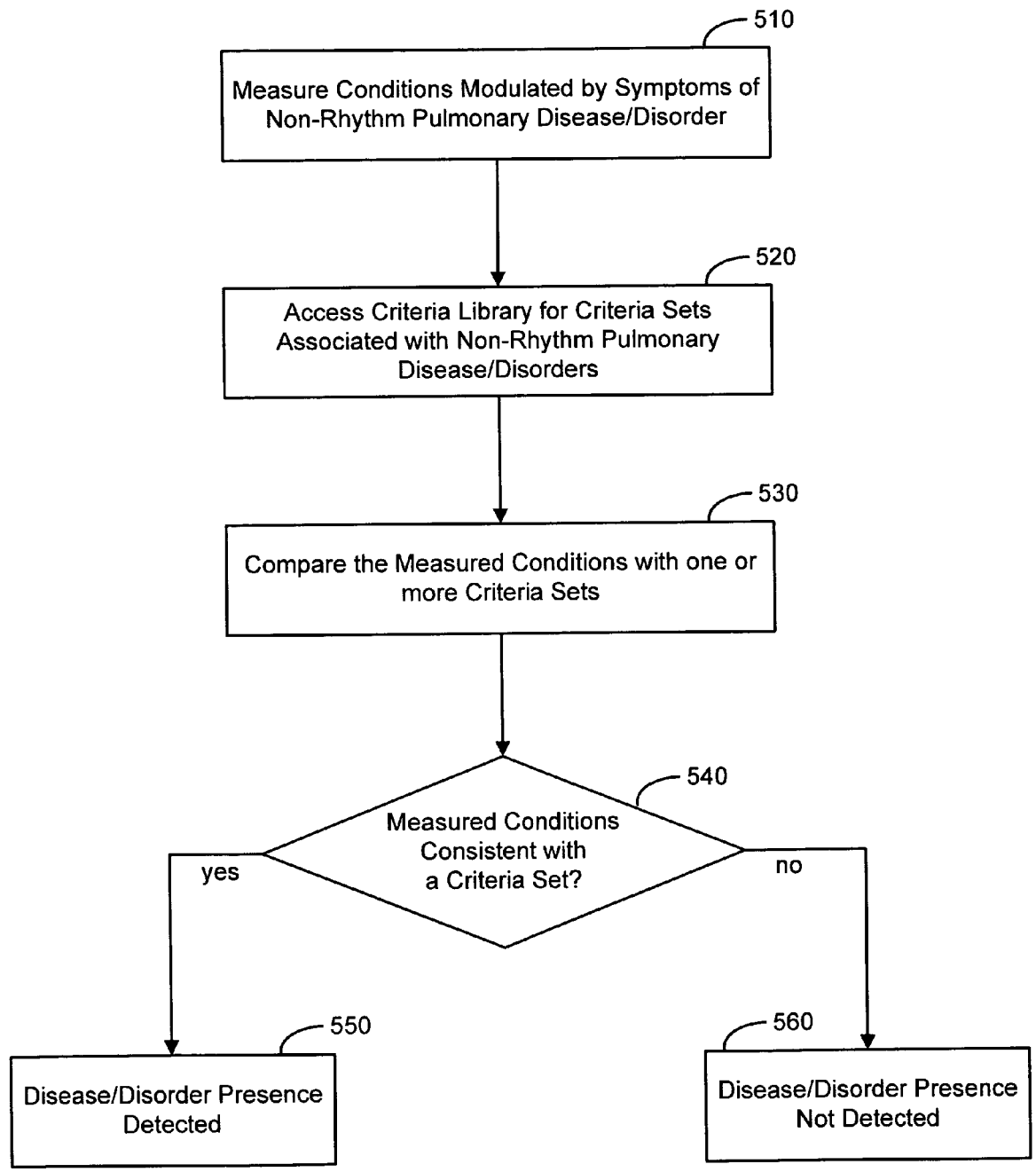
FIGS. 5A-5B are flowcharts illustrating methods of assessing a presence of a non-rhythm pulmonary disease in accordance with embodiments of the invention.

FIG. 5A is a flowchart illustrating a method for assessing a presence of a non-rhythm pulmonary disease/disorder in accordance with embodiments of the invention. The processes of FIG. 5A may be implemented using system components and criteria sets such as those illustrated in FIGS. 4A-4K.

One or more conditions modulated by symptoms of a non-rhythm pulmonary disease/disorder are measured 510. The conditions may be sensed by a sensing system of a respiratory therapy device, and optionally, by a sensing system of another medical device, such as a cardiac rhythm management device. A diagnosis processor receives the measured conditions and accesses 520 a criteria library. The diagnostic unit compares 530 the measured conditions with the one or more criteria sets.

If the measured conditions are consistent 540 with a particular criteria set, the presence of the non-rhythm pulmonary disease/disorder associated with the particular criteria set is detected 550. If the If the measured conditions are not consistent 540 with a particular criteria set, the presence of the non-rhythm pulmonary disease/disorder associated with the particular criteria set is not detected 560.

According to some embodiment, the system may monitor the non-rhythm pulmonary disease/disorder. Monitoring the progression of the disease/disorder may include periodically measuring the conditions relevant to the disease/disorder and storing information relevant to the disease/disorder. The periodically measured conditions may be used to monitor the severity of the disease, disease onset, symptoms or physiological changes during the course of the disease, disease regression, disease offset, and/or other aspects of the disease.

Figure 5B:
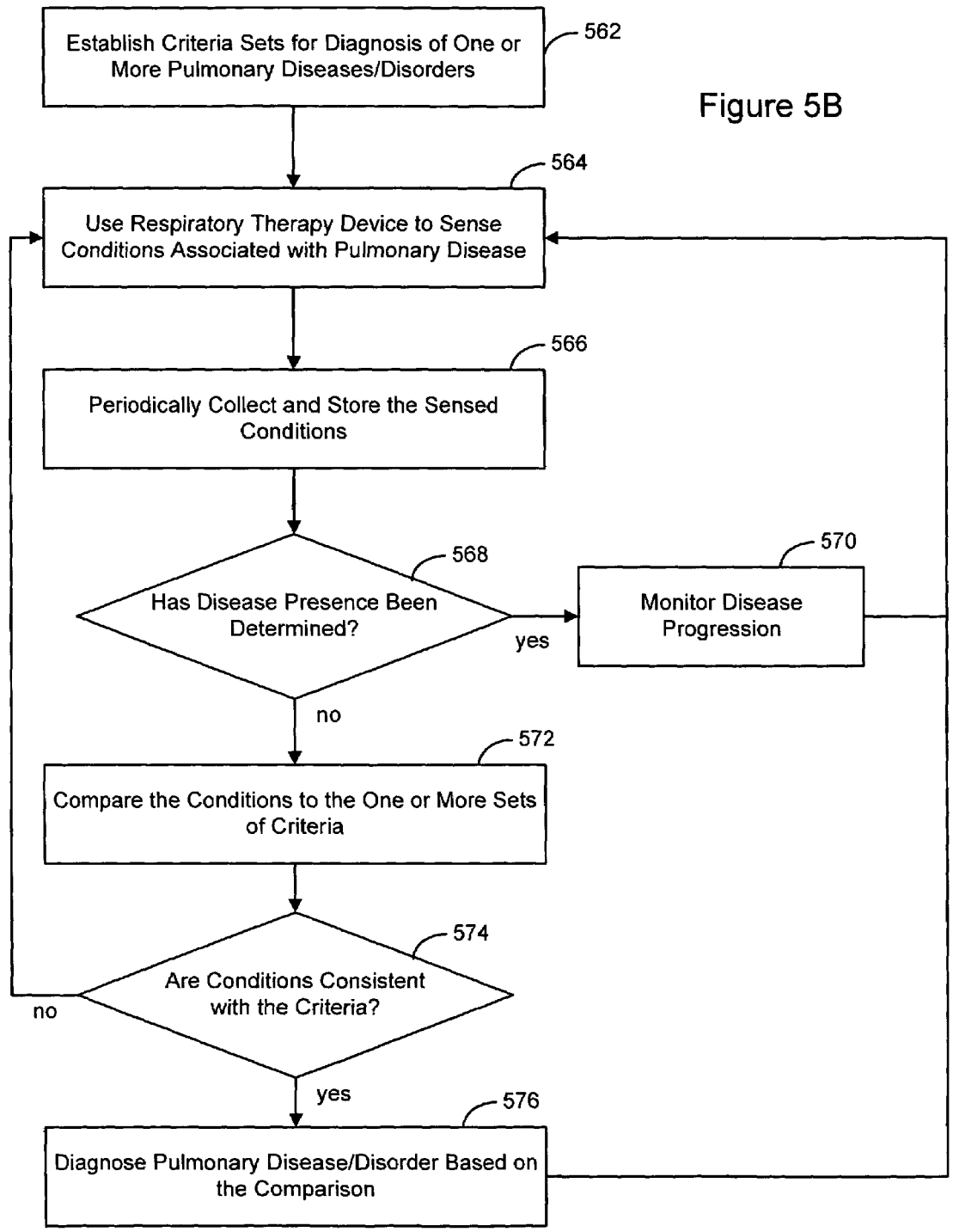

FIG. 5B is a flowchart illustrating a method of monitoring a presence of a non-rhythm pulmonary disease in accordance with embodiments of the invention. Criteria sets for assessment of the non-rhythm pulmonary diseases are established 562. A respiratory therapy device such as a CPAP device is used 564 to sense conditions modulated by disease symptoms. The sensor information may be gathered periodically 566, e.g., nightly, and stored for evaluation. If a presence of the disease was previously determined 568, then the progression of the disease may be monitored 570 based on the conditions used to determine a presence of the disease, or other conditions.

If a presence of the disease was not previously determined 568, then the levels of the sensed conditions are compared 572 to a set of criteria associated with the disease. If levels of the conditions are consistent 574 with the threshold levels, then the presence of the disease is determined 576. If levels of the conditions are not consistent 570 with the threshold levels, then the system continues 564 to sense conditions modulated by disease symptoms.

A number of the examples presented herein involve block diagrams illustrating functional blocks used for monitoring functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method for assessing a presence of a pulmonary disease other than a breathing rhythm disorder, comprising:
   detecting sleep-disordered breathing;
   delivering a disordered breathing therapy with a respiratory therapy device based on the detection of sleep-disordered breathing;
   sensing one or more conditions associated with a non-rhythm pulmonary disease using the respiratory therapy device;
   assessing the presence of the non-rhythm pulmonary disease based on the one or more sensed conditions; and
   adjusting the disordered breathing therapy based on the assessment of the presence of the non-rhythm pulmonary disease.

2. The method of claim 1, wherein sensing the one or more conditions comprises sensing respiratory pressure.

3. The method of claim 1, wherein sensing the one or more conditions comprises sensing respiratory flow.

4. The method of claim 1, wherein sensing the one or more conditions comprises detecting a percentage of an exhaled gas.

5. The method of claim 1, wherein assessing the presence of the non-rhythm pulmonary disease comprises assessing the presence of an obstructive pulmonary disease.

6. The method of claim 1, wherein assessing the presence of the non-rhythm pulmonary disease comprises assessing the presence of a restrictive pulmonary disease.

7. The method of claim 1, wherein assessing the presence of the non-rhythm pulmonary disease comprises assessing the presence of a pulmonary vasculature disorder.

8. The method of claim 1, wherein assessing the presence of the non-rhythm pulmonary disease comprises assessing the presence of a pleural disorder.

9. The method of claim 1, wherein assessing the presence of the non-rhythm pulmonary disease comprises:
   comparing the one or more conditions to one or more sets of threshold criteria; and
   assessing the presence of the pulmonary disease based on the comparison.

10. The method of claim 1, further comprising monitoring a progression of the non-rhythm pulmonary disease.

11. A medical system, comprising:
    a respiratory therapy device, the respiratory therapy device comprising:
       a therapy unit configured to deliver a disordered breathing therapy to a patient;
       a sensor system configured to sense one or more conditions associated with sleep-disordered breathing and sense one or more conditions associated with a pulmonary disease other than a breathing rhythm disorder; and
    a diagnosis unit coupled to the sensor system, the diagnosis unit comprising a controller and memory, the controller configured to execute program instructions stored in the memory to cause the medical system to detect sleep-disordered breathing based on the sensed one or more conditions associated with sleep-disordered breathing, control delivery of the disordered breathing therapy based on the detection of sleep-disordered breathing, assess a presence of the non-rhythm pulmonary disease based on the one or more sensed conditions associated with the non-rhythm pulmonary disease, and adjust delivery of the disordered breathing therapy based on the assessed presence of the non-rhythm pulmonary disease.

12. The system of claim 11, wherein the respiratory therapy device comprises a positive airway pressure device.

13. The system of claim 11, wherein the sensor system comprises an airflow sensor.

14. The system of claim 11, wherein the sensor system comprises a pressure sensor.

15. The system of claim 11, wherein the sensor system comprises a gas sensor configured to sense a percentage of exhaled $CO_2$.

16. The system of claim 11, wherein the sensor system comprises a gas sensor configured to sense a percentage of exhaled $O_2$.

17. The system of claim 11, further comprising a criteria library within the memory configured to store one or more sets of threshold criteria, wherein the controller is configured to execute stored program instructions to cause the medical system to compare the one or more conditions associated with the non-rhythm pulmonary disease to the one or more sets of threshold criteria and assess the presence of the pulmonary disease based on the comparison.

18. The system of claim 11, wherein the memory further stores program instructions executable by the controller to cause the medical system to store periodically collected information associated with the one or more conditions and assess the presence of the non-rhythm pulmonary disease based on the periodically collected information.

19. The system of claim 11, further comprising:
an additional sensor system coupled to the diagnosis unit, the additional sensor system configured to sense one or more additional conditions associated with the non-rhythm pulmonary disease; and
wherein the controller of the diagnosis unit is further configured to execute stored program instructions to cause the medical system to assess the presence of the non-rhythm pulmonary disease based on the one or more additional conditions.

20. A system for diagnosing a pulmonary disease other than a breathing rhythm disorder, comprising:
means for detecting sleep-disordered breathing;
means for delivering a disordered breathing therapy with a respiratory therapy device based on the detection of sleep-disordered breathing;
means for sensing one or more conditions associated with a non-rhythm pulmonary disease using the respiratory therapy device;
means for assessing a presence of the non-rhythm pulmonary disease based on the one or more conditions; and
means for adjusting the disordered breathing therapy based on the assessment of the presence of the non-rhythm pulmonary disease.

21. The system of claim 20, further comprising means for storing periodically collected information associated with the one or more conditions, wherein the means for assessing the presence of the pulmonary disease comprises means for assessing the presence of the non-rhythm pulmonary disease based on the stored information.

22. The system of claim 20, further comprising:
means for detecting an additional one or more conditions associated with the non-rhythm pulmonary disease using one or more additional devices; and
means for assessing the presence of the pulmonary disease based on the one or more additional conditions.

23. The method of claim 1, wherein the disordered breathing therapy is a sleep disordered breathing therapy.

24. The system of claim 11, wherein the disordered breathing therapy deliverable by the therapy unit is a sleep disordered breathing therapy.

25. The system of claim 20, wherein the means for delivering the disordered breathing therapy comprises means for delivering a sleep disordered breathing therapy.

* * * * *

UNITED STATES PATENT AND TRADEMARK OFFICE
CERTIFICATE OF CORRECTION

PATENT NO.      : 7,575,553 B2  Page 1 of 1
APPLICATION NO. : 10/930508
DATED           : August 18, 2009
INVENTOR(S)     : Stahmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1109 days.

Signed and Sealed this

Fourteenth Day of December, 2010

David J. Kappos
*Director of the United States Patent and Trademark Office*